United States Patent

Iglesias et al.

[11] Patent Number: 5,951,504
[45] Date of Patent: Sep. 14, 1999

[54] ANKLE BRACE WITH ADJUSTABLE HEEL STRAP

[75] Inventors: Joseph M. Iglesias, Thousand Oaks, Calif.; Tracy E. Grim, Tulsa, Okla.; William K. Arnold, Longmeadow, Mass.; Eric E. Johnson, Encinitas; Michael Skahan, Camarillo, both of Calif.

[73] Assignee: Royce Medical Products, Camarillo, Calif.

[21] Appl. No.: 09/021,497

[22] Filed: Feb. 10, 1998

Related U.S. Application Data

[63] Continuation-in-part of application No. 08/521,091, Aug. 29, 1995, Pat. No. 5,716,335, which is a continuation-in-part of application No. 08/099,237, Jul. 29, 1993, Pat. No. 5,445,602.

[51] Int. Cl.$^6$ .......................................... A61F 5/00
[52] U.S. Cl. ................................. 602/27; 602/16
[58] Field of Search ............................ 602/5, 23, 27–29, 602/16

[56] References Cited

U.S. PATENT DOCUMENTS

| | | |
|---|---|---|
| 3,834,377 | 9/1974 | Lebold . |
| 4,821,743 | 4/1989 | Wetz . |
| 4,834,078 | 5/1989 | Biedermann . |
| 4,964,402 | 10/1990 | Grim et al. . |
| 4,977,891 | 12/1990 | Grim . |
| 5,014,691 | 5/1991 | Cueman et al. . |
| 5,031,607 | 7/1991 | Peters . |
| 5,044,360 | 9/1991 | Janke . |
| 5,069,202 | 12/1991 | Prock . |
| 5,088,480 | 2/1992 | Wang . |
| 5,094,232 | 3/1992 | Harris et al. . |
| 5,209,722 | 5/1993 | Miklaus et al. . |
| 5,226,875 | 7/1993 | Johnson . |
| 5,242,378 | 9/1993 | Baker . |
| 5,242,379 | 9/1993 | Harris et al. . |
| 5,366,439 | 11/1994 | Peters . |
| 5,445,602 | 8/1995 | Grim et al. . |
| 5,445,603 | 8/1995 | Wilkerson . |
| 5,472,411 | 12/1995 | Montag et al. . |
| 5,501,659 | 3/1996 | Morris et al. . |
| 5,527,269 | 6/1996 | Reithofer . |
| 5,716,335 | 2/1998 | Iglesias et al. . |

*Primary Examiner*—Richard J. Apley
*Assistant Examiner*—Kim M. Lee
*Attorney, Agent, or Firm*—Oppenheimer Wolff & Donnelly LLP

[57] ABSTRACT

An improved ankle brace that is easily adjustable for improved comfort and use. The ankle brace includes a pair of relatively rigid side supports to fit about a lower leg of a patient, and the lower area of the side supports may be adapted to position an assembly of heel straps. The assembly may include at least two straps, which are coupled at the ends and adapted to adjust the effective length of the assembly, so that it may be accommodated for different heel widths of different patients. Alternatively, the assembly may include three pieces, an intermediary member for linking the other two straps. The assembly may be attached to the side supports through a pin mechanism that may be either capped (as by heat staking) or welded at the end to hold it in position. Alternatively, a cap with protruding plastic pin may be molded directly onto the strap, effectively making them one piece to be assembled as such. Also, the assembly is preferably made of flexible resilient material so that it will comfortably conform to patient's heel, but be resistant to stretching.

29 Claims, 15 Drawing Sheets

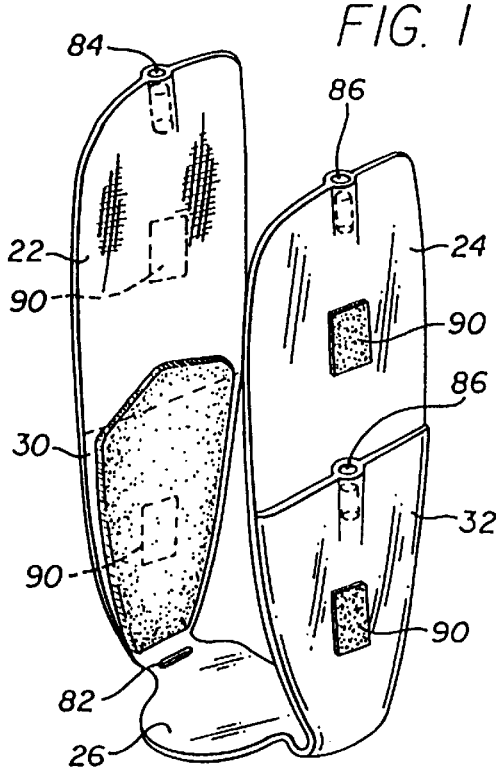
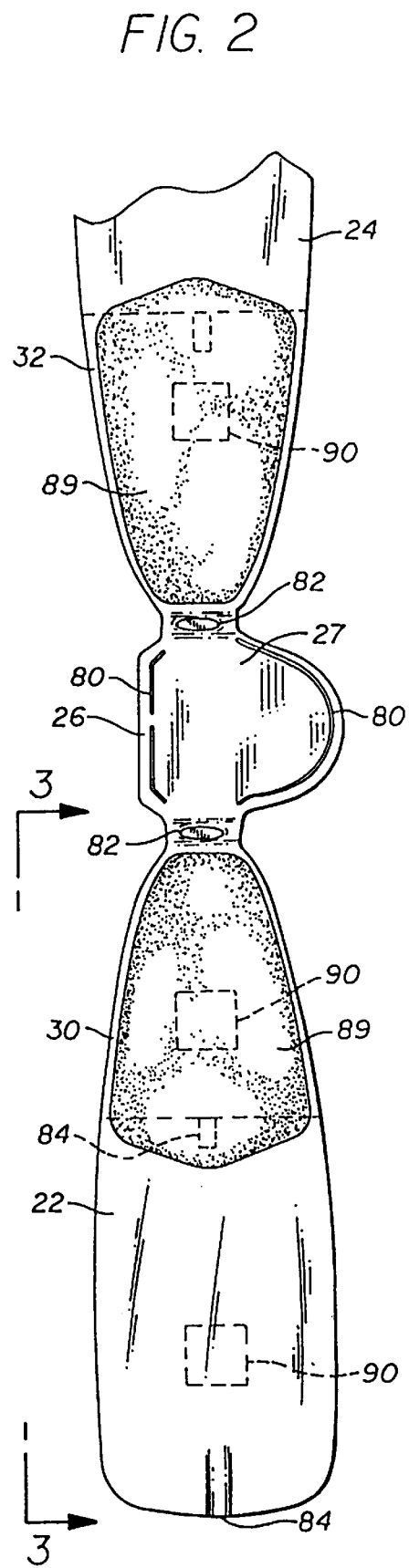
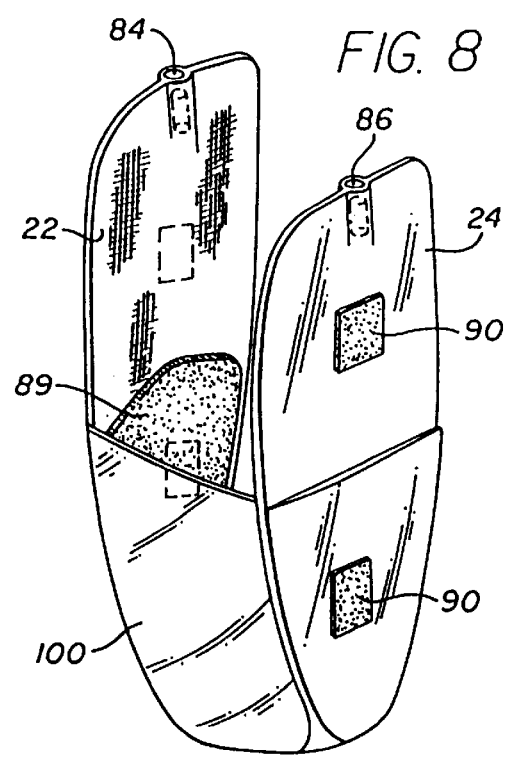

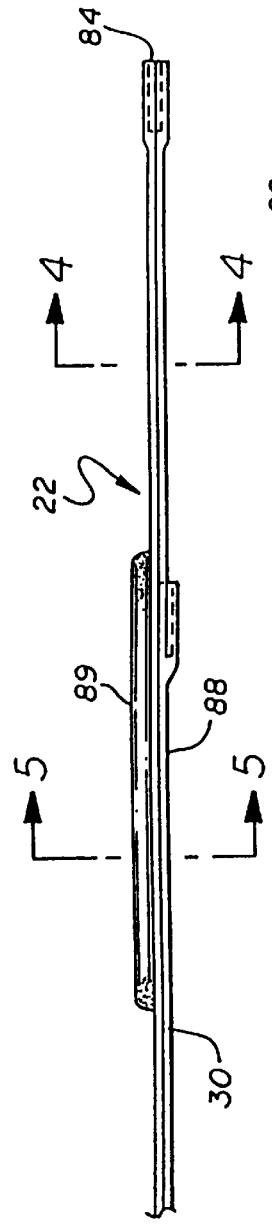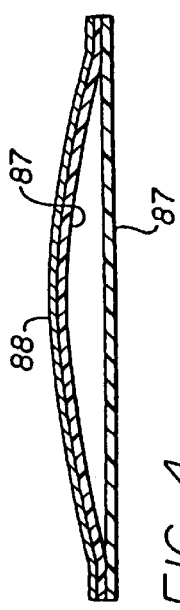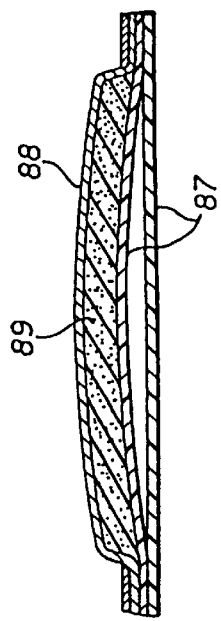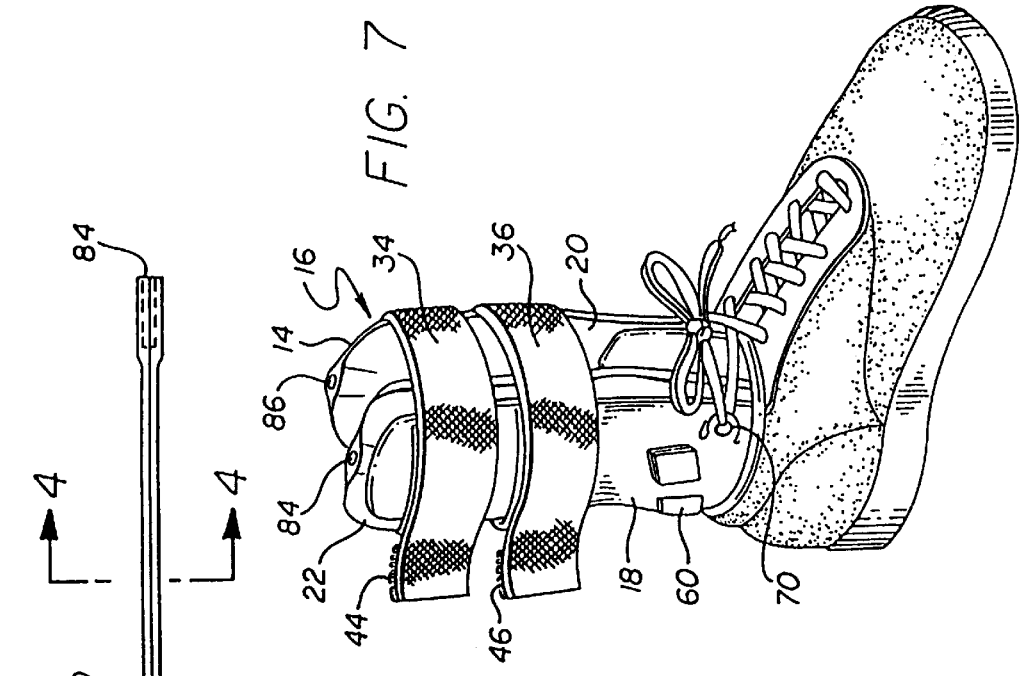

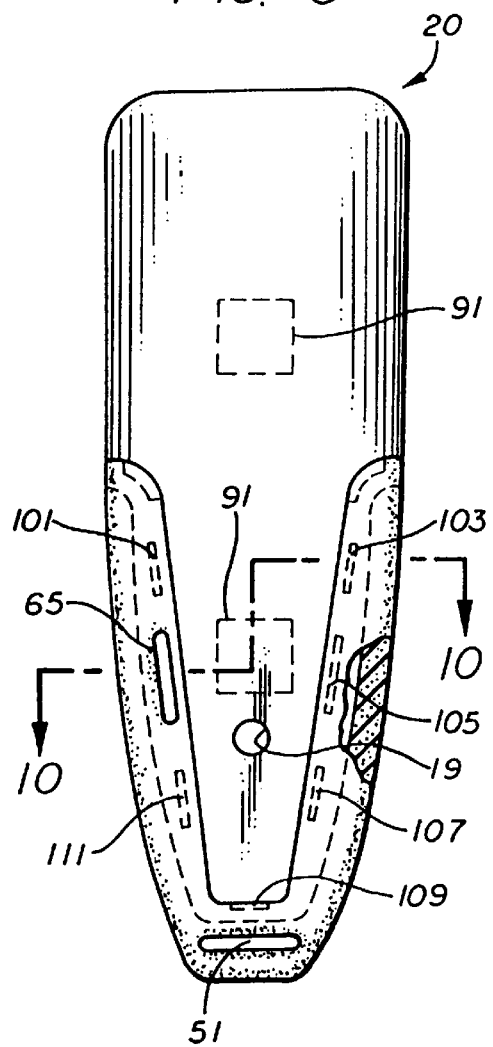
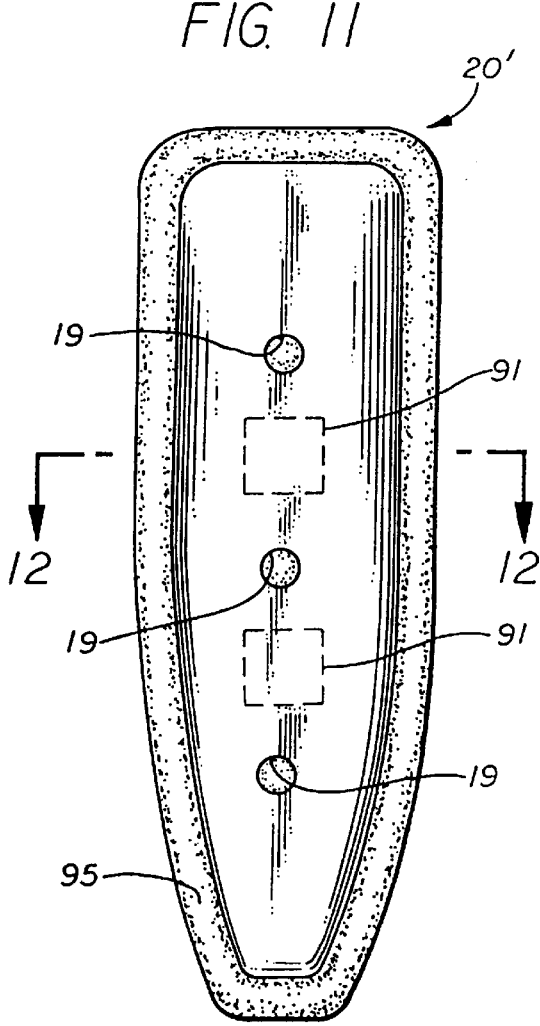
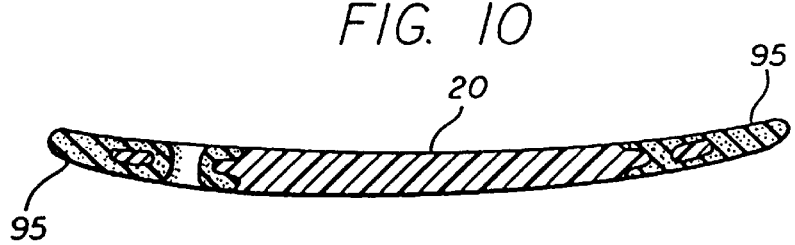
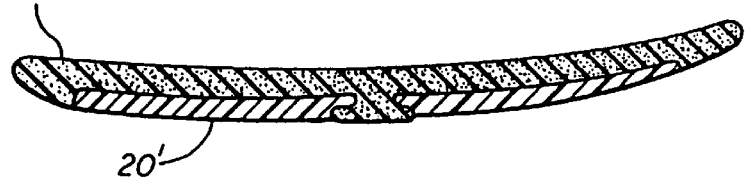

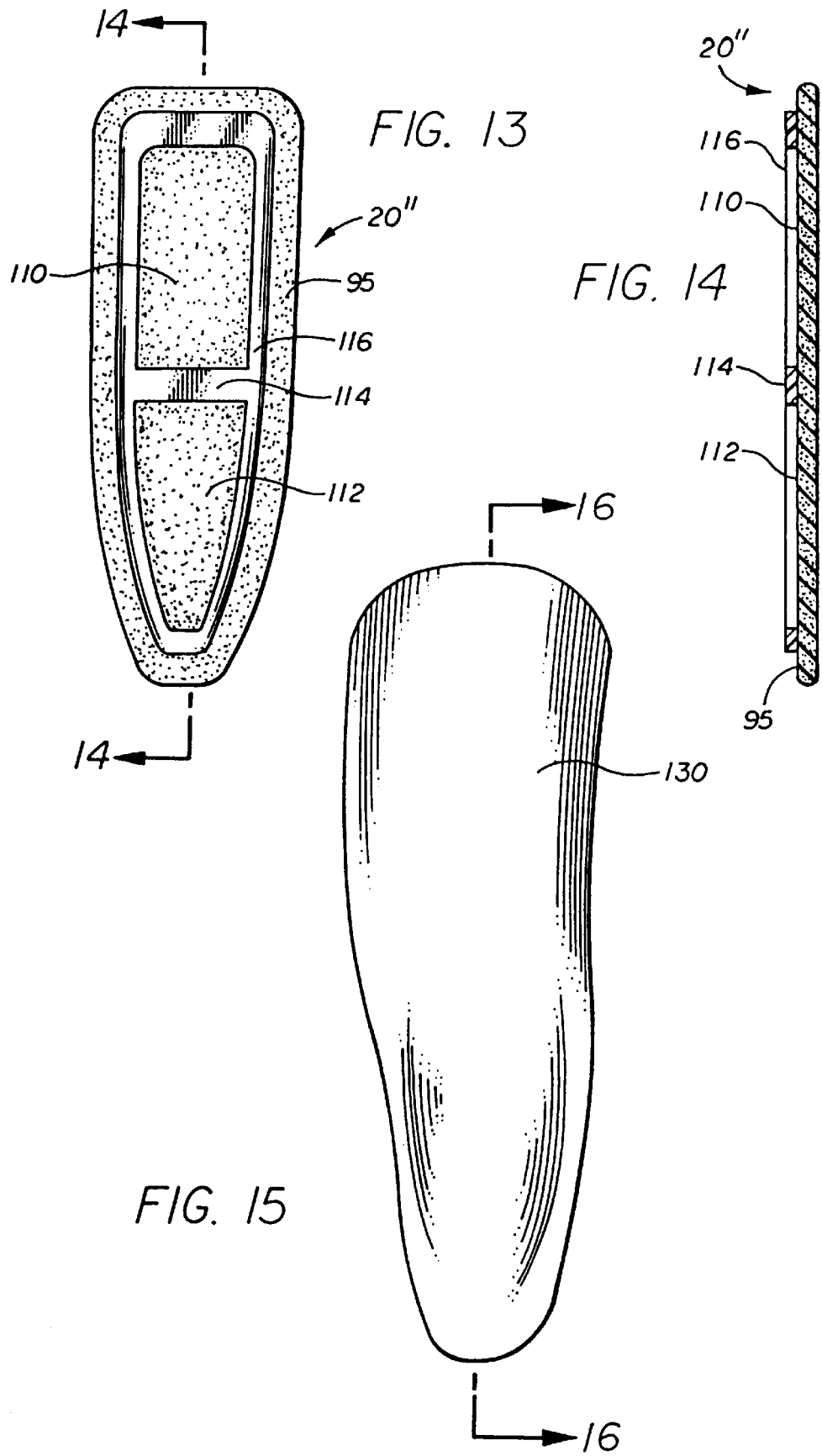

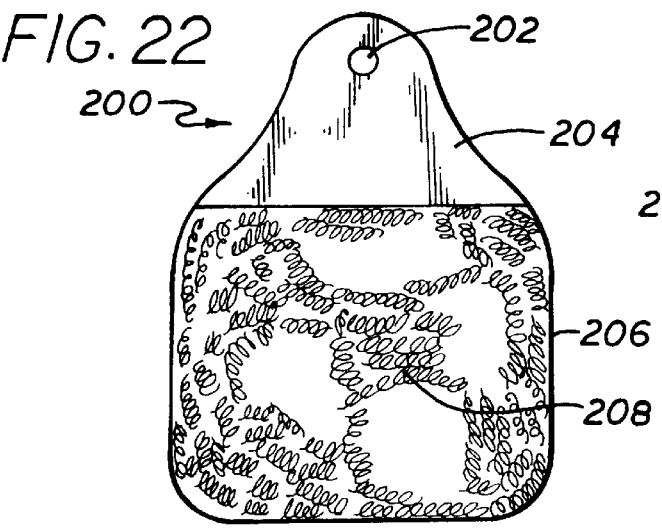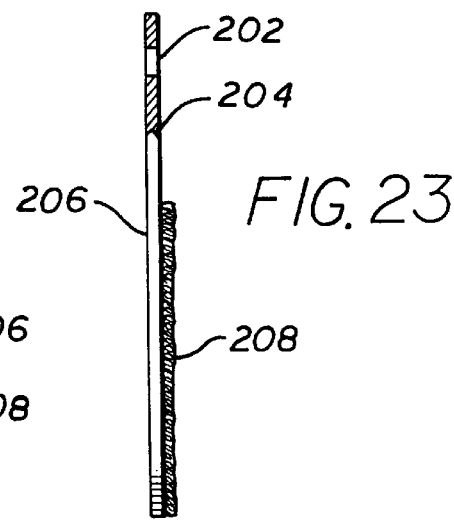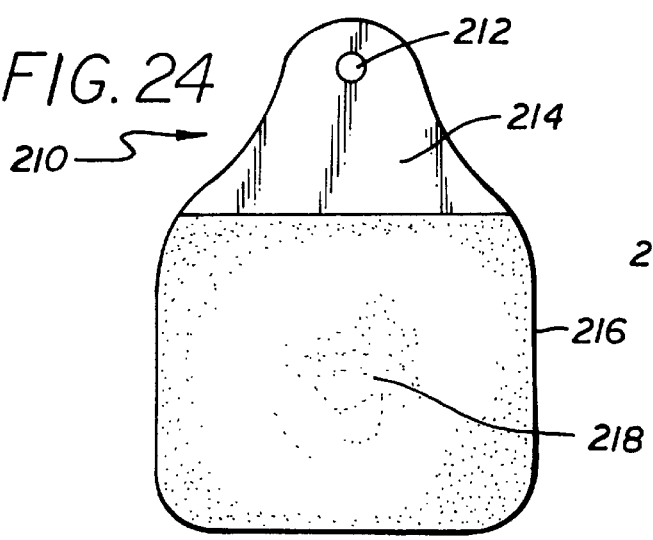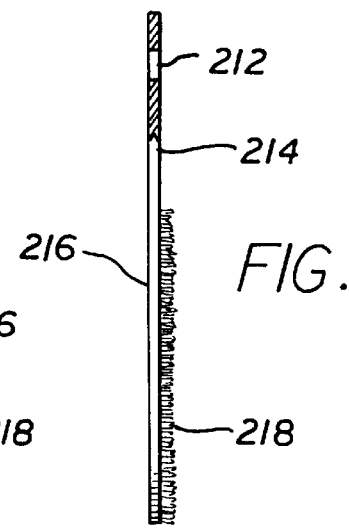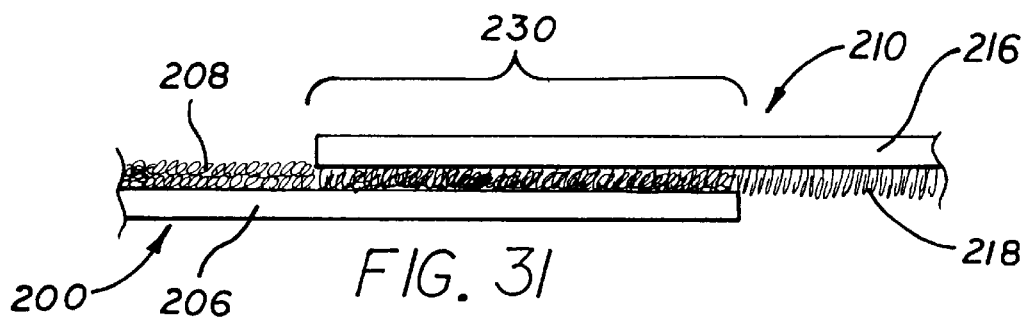

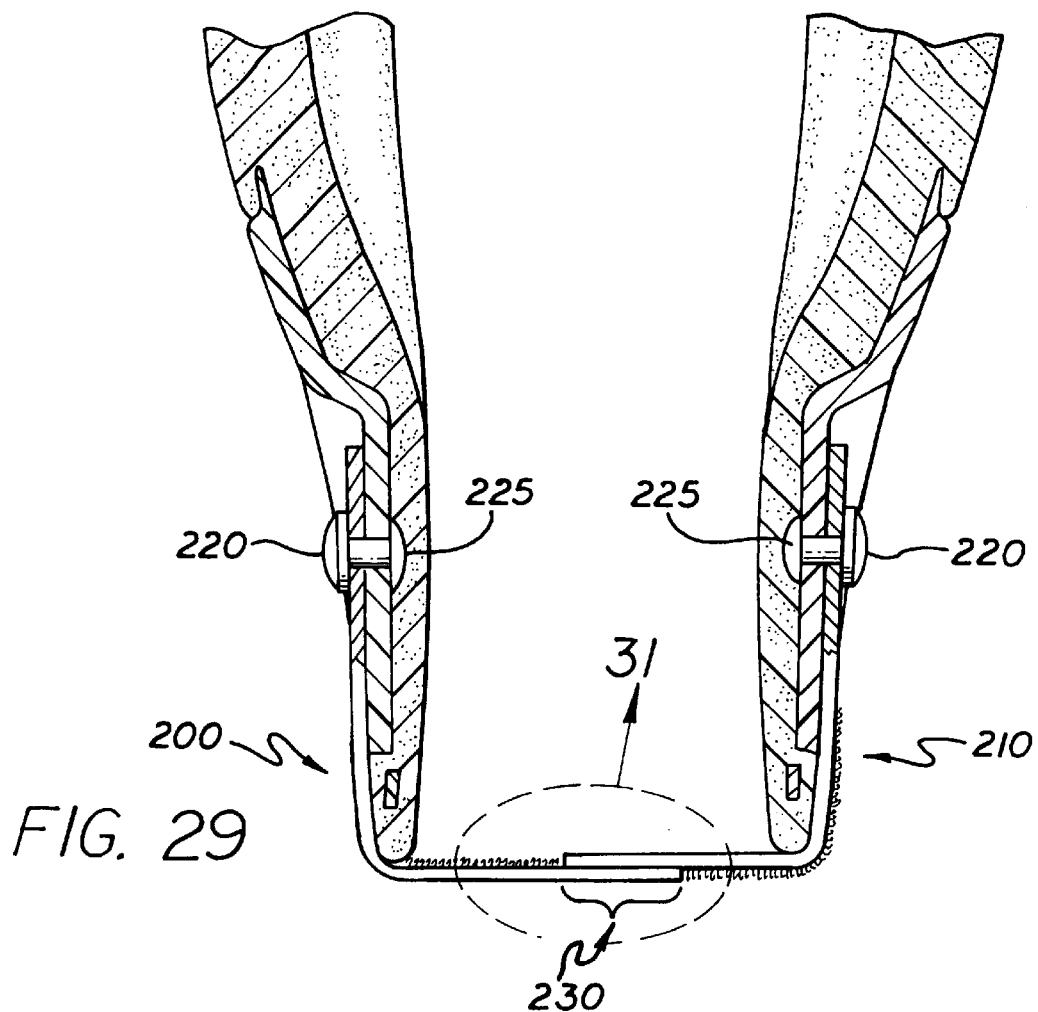
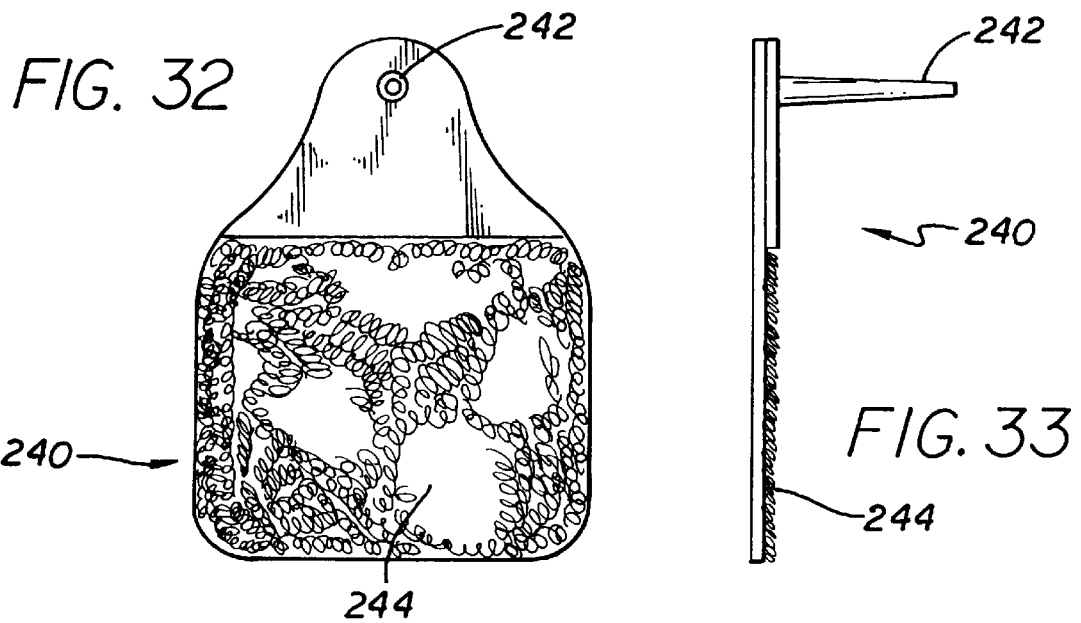

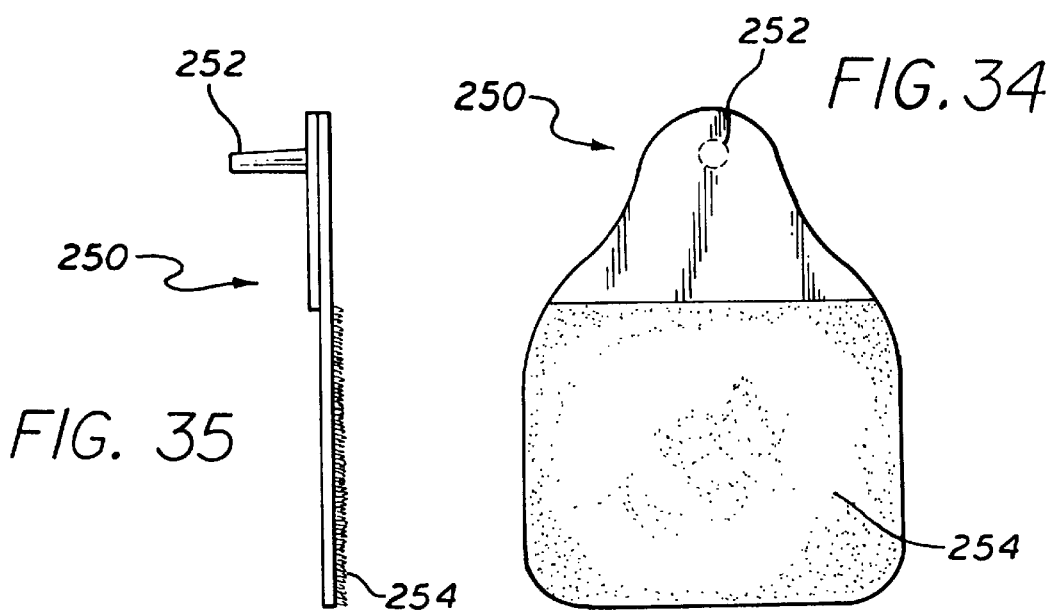
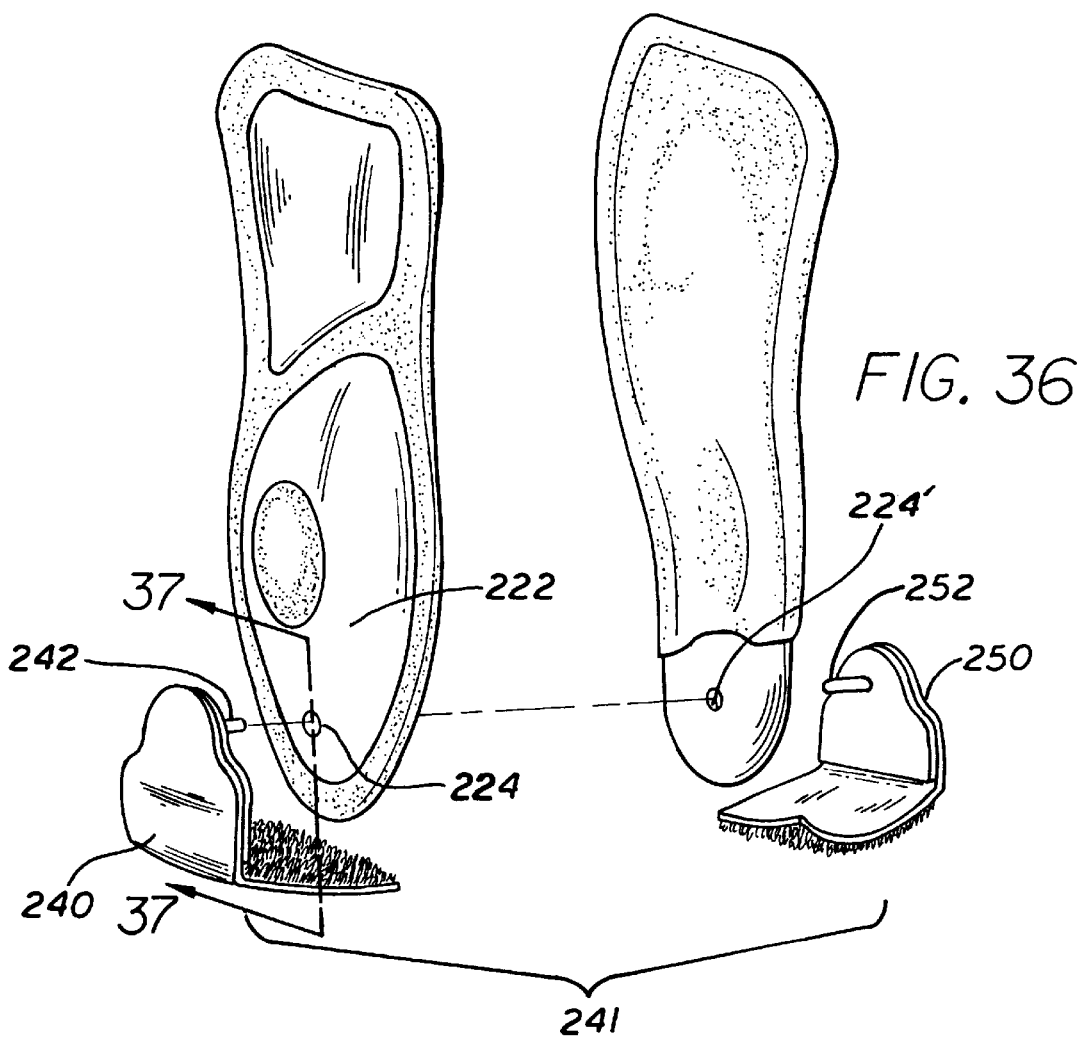

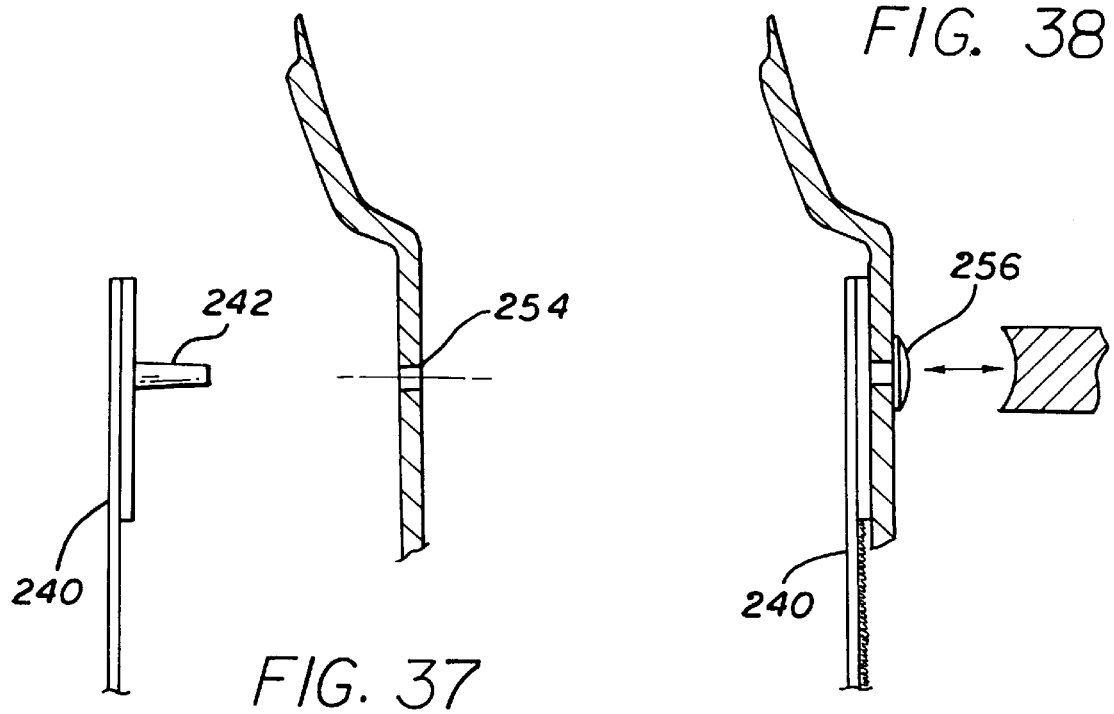
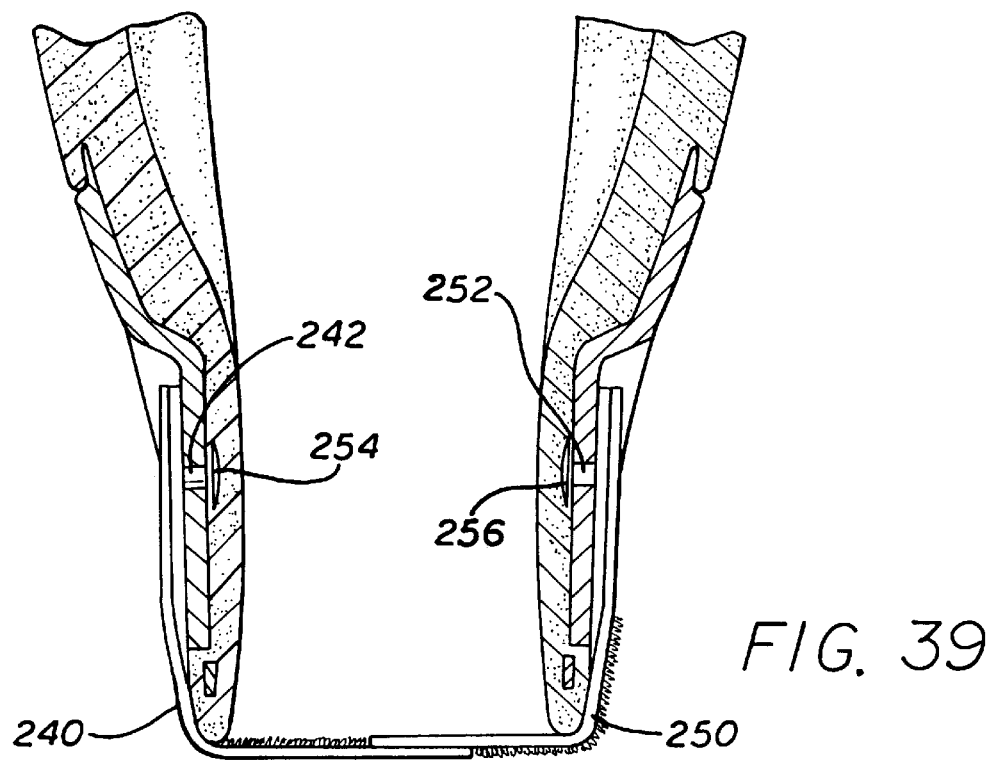

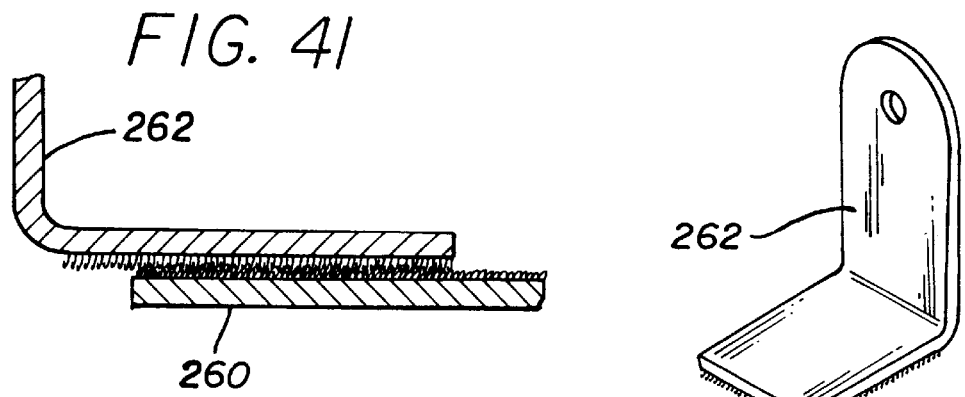
FIG. 41
FIG. 40
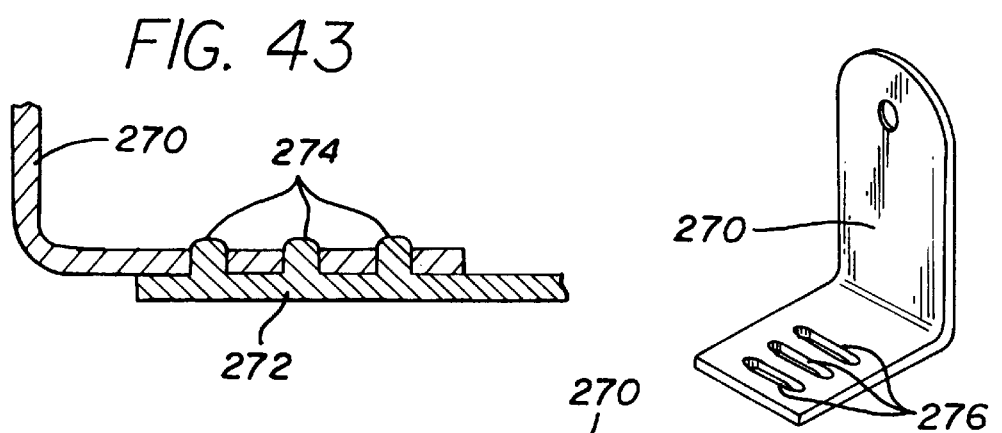
FIG. 43
FIG. 42

ANKLE BRACE WITH ADJUSTABLE HEEL STRAP

CROSS-REFERENCE TO RELATED APPLICATIONS

This is a continuation-in-part of application Ser. No. 08/521,091, filed Aug. 29, 1995, issuing Feb. 10, 1998, as U.S. Pat. No. 5,716,335, and which is a continuation-in-part of application Ser. No. 08/099,237, filed Jul. 29, 1993, now U.S. Pat. No. 5,445,602, issued Aug. 29, 1995. The entire contents of both of these application are hereby incorporated by reference.

BACKGROUND OF THE INVENTION

The present invention relates to ankle braces for stabilizing ankles before or after injury. In particular, the ankle brace of the present invention stabilizes the ankle against inversion and eversion and anterior subluxation, while allowing normal dorsiflexion and plantarflexion movement.

After injury to an ankle, such as a fracture or severe ankle sprain, it is often necessary to completely immobilize the injured ankle through the use of a molded plaster or resin cast. Once the injury has been stabilized, however, recovery may be accelerated by removing the molded plaster or resin cast and replacing it with a removable ankle brace so that the ankle can be exercised while healing. Even if the injury is not severe enough to warrant complete immobilization of the ankle, it is still sometimes necessary to use a functional wailing brace to stabilize the ankle against inversion (the foot rolling inward), eversion (the foot rolling outward) and/or subluxation (partial dislocation), while still allowing the normal dorsiflexion and plantarflexion movement of the ankle.

A variety of ankle braces, walking casts and other orthopedic ankle apparatuses have previously been proposed. For instance, in U.S. Pat. No. 4,977,891, to Tracy E. Grim, an ankle brace comprising two relatively rigid side supports with inflatable bladders attached to them is described. Other ankle braces including air inflatable bladders are shown in Glenn W. Johnson, Jr.'s U.S. Pat. Nos. 4,280,489 and 4,628,945. These prior art devices proposed by Johnson are intended to be worn within a separate shoe and are also inflatable.

Thermal treatment has been available with the use of orthopedic gel pads which tend to mold themselves to fit the area they are applied to, providing a level of comfort and padding as well as providing thermal treatment of the affected area. One such pad is shown in U.S. Pat. No. 5,027,801.

Prior art walking braces have employed rigid support shells, which may engage and irritate, pinch and damage the skin within the shoe. For instance, the rigid ankle brace shown by the U.S. Pat. No. 4,834,078 is made of "high-performance composite material."

U.S. Pat. No. 5,445,602 shows two relatively rigid side supports, where the area adjacent to the ankle is covered with a flexible or resilient material. A strap is attached to the lower ends of both side supports to tie them together.

SUMMARY OF THE INVENTION

In accordance with one broad aspect of this invention, the outer edge portions of at least the lower area of the side supports, adjacent to the ankle, are formed of a flexible material.

In accordance with another broad aspect of this invention, each entire side support is bonded to or integrally associated with flexible material, slightly larger in size but similar in shape to the side support. Both of these side support designs improve the fit and the comfort of the brace around the user's lower leg.

In accordance with yet another broad aspect of this invention, a more flexible material is formed around a more rigid material. In an alternative implementation, the more flexible material is formed with protrusions/tabs and/or receptacles for protrusions/tabs formed in the more rigid material. This allows the more flexible material and more rigid material to be mated and interlocked to one another.

In accordance with another broad aspect of this invention, the more rigid material is hollowed out in certain areas to form a frame. The frame is covered with the more flexible material and the resultant structure is employed as an ankle brace.

Accordingly, it is a primary object of the present invention to prevent undesired inversion, eversion and anterior subluxation while allowing plantarflexion and dorsiflexion of the ankle, without irritating or pinching the skin.

Another object of this invention is to provide a more comfortable ankle brace, which will firmly support an injured lower leg. As discussed above, this may be achieved by a combination of more and less flexible materials, using rigid or semi-rigid structural frame supporting the flexible resilient material. In addition, this may be achieved by designing the rigid structural frame such that hollowed out portions thereof correspond to the ankle or malleolus area. Such design of the structure frame will allow the protruding ankle to be covered only by the flexible material while the surrounding frame provides the necessary support and control, thus increasing the comfort and effectiveness of the brace.

Yet another goal of this invention is to accommodate various sizes and widths of feet by providing a flexible heel strap, the effective length of which can be adjusted. Further, the flexible heel strap may be pivotally attached to the bottom of the side support, thus improving the plantarflexion and dorsiflexion of the ankle, while still limiting lateral movement. The pivot structure is preferably in the form of a rotatable pivot disc, to which the strap may be adjustably secured.

An improved ankle brace pursuant to this invention may have two relatively rigid side supports, the outer edge portion of the lower area of the side supports, adjacent to the ankle being covered with a flexible or resilient material. The flexible resilient material may be permanently secured to the side supports by bonding, mechanical interlocking or any other suitable arrangements. Additional resilient flexible material may be placed on the interior surface of the side supports to improve the fit and comfort of the brace around the user's lower leg. The rigid side supports may be of an open type with the resilient flexible material extending across the side supports and beyond the edges thereof. The lower area of the side supports may include a pivoting mechanism to adjustably receive heel straps. Each of the side supports may include a structural frame that surrounds but does not cover the ankle or malleolus.

Alternatively, an assembly of flexible heel straps incorporating a pin mechanism may be pivotally attached to the lower area of the side supports. The flexible heel straps have their effective lengths being adjustable to accommodate for different heel widths of different patients and/or different fits. The assembly may include at least two straps, each strap may be adapted so each strap's end may be coupled to one another. The coupling may take place through a VELCRO hook and loop pads on the coupling ends, or through a series of upright elements at one end and a series of openings at the other end being releasably snap-fit married together.

The foregoing and other features and advantages of the present invention as well as a more complete understanding thereof will be made apparent from a consideration of the following detailed description in connection with the accompanying drawings.

BRIEF DESCRIPTION OF THE DRAWINGS

FIG. 1 is a diagrammatic, perspective view of a bladder and pump arrangement for an ankle brace;

FIG. 2 is a partial unfolded top plan view of the inside surface of the bladder and pump arrangement of FIG. 1;

FIG. 3 is a partial side view of the bladder and pump arrangement taken on line 3—3 of FIG. 2;

FIG. 4 is a cross-sectional view of one of the main bladders taken along line 4—4 of FIG. 3;

FIG. 5 is a cross-sectional view of one of the additional bladders and a cushioning member of the bladder taken along line 5—5 of FIG. 3;

FIG. 7 is a perspective view of an embodiment of the ankle brace of the present invention fitted and properly secured in association with a shoe including laces;

FIG. 8 is diagrammatic, perspective view of another embodiment of a bladder and pump arrangement of the present invention;

FIG. 9 is a side view of a side support member illustrating the principles of the present invention;

FIG. 10 is a cross-sectional view of the side support taken along line 10—10 of FIG. 9;

FIG. 11 is a side view of a different embodiment of a side support member illustrating the principles of the present invention;

FIG. 12 is a cross-sectional view of the side support of FIG. 11 taken along line 12—12 of FIG. 11;

FIG. 13 is a side view of an alternative embodiment of a side support member of the present invention;

FIG. 14 is a cross-sectional view of the embodiment shown in FIG. 13;

FIG. 15 is a side view of an alternative embodiment of a side support member of the present invention;

FIG. 22 is a plan view of one of the flexible heel straps with a region of VELCRO loop pad of another embodiment of the present invention;

FIG. 23 is a side view of the strap shown in FIG. 22;

FIG. 24 is a plan view of another of the flexible heel straps with a region of VELCRO hook pad of the embodiment of FIG. 22;

FIG. 25 is a side view of the strap shown in FIG. 24;

FIG. 29 is an enlarged cross-sectional view taken along line 29—29 of FIG. 28;

FIG. 31 is an enlarged view taken on circle 31 of FIG. 29;

FIG. 32 is a plan view of another flexible heel strap with a region of VELCRO-type loop pad having a protruding pin;

FIG. 33 is a side view of the flexible heel strap of FIG. 32;

FIG. 34 is a plan view of another flexible heel strap with a region of VELCRO-type hook pad having a protruding pin;

FIG. 35 is a side view of the flexible heel strap of FIG. 34;

FIG. 36 is an exploded perspective view of the embodiment of FIGS. 32 and 34 showing the side supports and heel straps in their relative positions;

FIG. 37 is an exploded cross-sectional view illustrating a heel strap coupling to a side support of FIG. 36;

FIG. 38 is a cross-sectional view of the protruding pin being ultrasonically welded;

FIG. 39 is an enlarged cross-sectional view of the side supports and heel straps that are assembled;

FIG. 40 is a perspective view of a still further alternative embodiment of heel straps of the present invention;

FIG. 41 is a cross-sectional view taken along line 41—41 of FIG. 40;

FIG. 42 is a perspective view of another alternative embodiment of heel straps of the present invention; and FIG. 43 is an enlarged cross-sectional view taken along line 43—43 of FIG. 42.

DETAILED DESCRIPTION OF PREFERRED EMBODIMENTS OF THE INVENTION

Initially, it is noted that the drawings in the present case disclose a number of inventions, with one invention being described in detail in connection with FIGS. 7 and 9–18. FIGS. 1–8 are included for explanatory purposes as disclosing a complete ankle support assembly as shown in FIG. 7. The embodiments of FIGS. 9–18, illustrating principles of this invention, may be used as side supports 18, 20 in the configuration of FIG. 7. A second invention is described in detail in FIGS. 22–43. While FIGS. 22–29 describe a flexible heel strap assembly, FIGS. 30–43 show the alternative means of coupling the flexible heel strap assembly to the ankle side support assembly.

Figure 6:
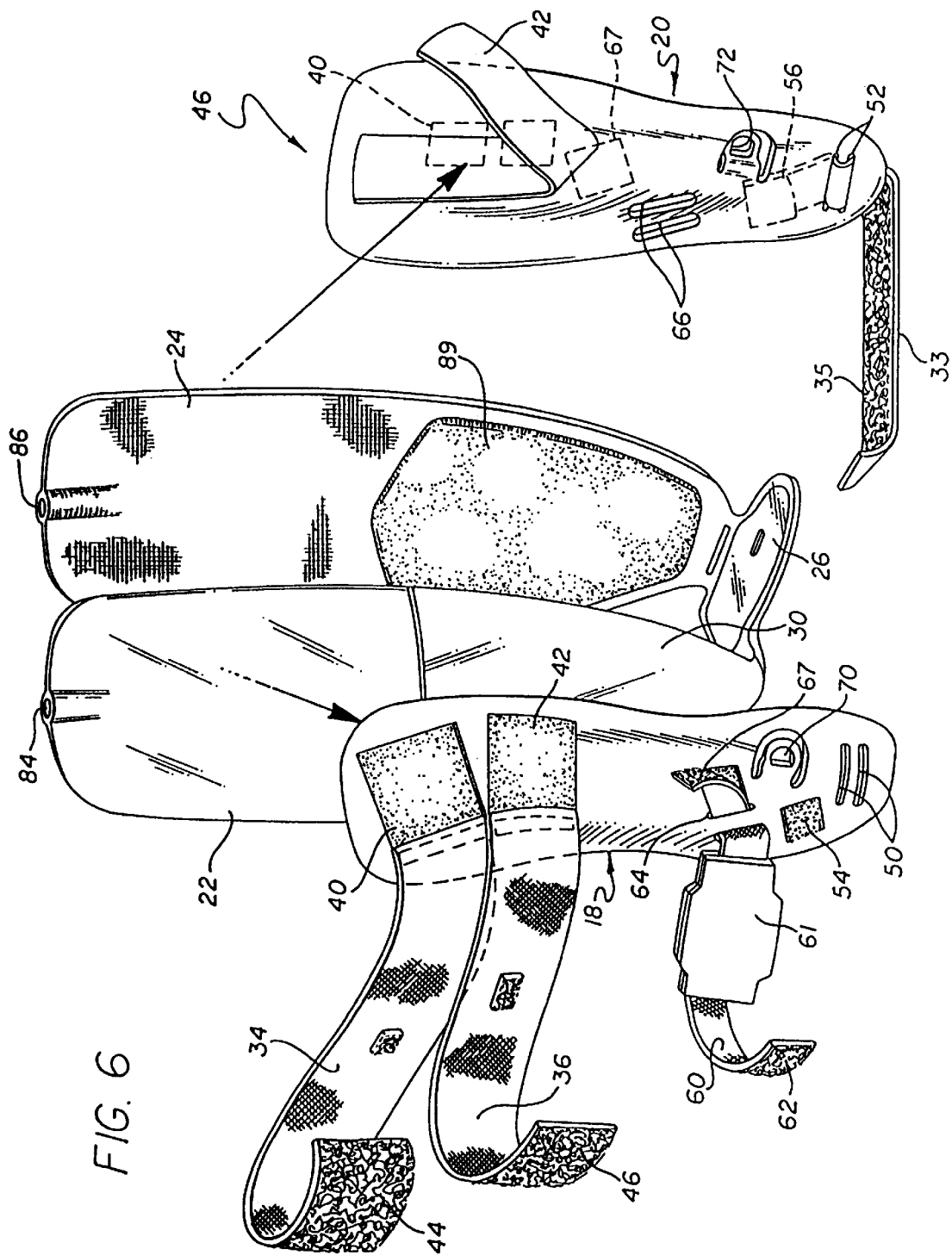
FIG. 6 is an exploded perspective view of an embodiment of an improved ankle brace.

With reference to FIGS. 6 and 7, an improved ankle brace 16 includes a pair of side support members 18 and 20 preferably made of injection molded plastic, for example, nylon or rigid polypropylene, having sufficient thickness and other properties so that they are relatively stiff or rigid. They are shaped so as to fit about the lower leg and ankle and are approximately eight to ten inches long. Also included are two main inflatable bladders 22 and 24 and a pump 26 which are interconnected and formed with one welding process. The inflatable bladders 22 and 24 can be attached to the side supports 18 and 20 using a VELCRO fabric, double-sided adhesive or any other suitable means. Additional inflatable bladders 30 and 32, as shown in FIGS. 1 and 2, are placed distally upon the main inflatable bladders 22 and 24.

Interconnecting the two side support members 18 and 20 is a bottom strap 33. The bottom strap 33 may include a surface 35 of VELCRO loop material and with the bottom strap being adjustable through the use of double openings 50 and 52 located near the bottom end of the side supports 18 and 20. The ends of the bottom strap 33 may be fixed in position with the use of additional VELCRO loop material 54 and 56 located on the outside of the side support members 18 and 20. Specifically, the adjustment is accomplished by positioning the ends of the strap 33 to extend from the outside of each support member 18 and 20 through opening 50 or 52 and then through the other one of the openings 50 or 52 and then attached by the VELCRO loop material 54. Thus, the proper distance may be easily adjusted between the side support members 18 and 20 at the lowermost portion.

The side supports 18 and 20 may be securely attached around the lower leg and ankle of the user just below the calf area using two strap members 34, 36. These strap members 34, 36 also include VELCRO portions 40 and 42 on their outer surfaces, and with VELCRO loop material 44 and 46 at the end portions of the straps 34 and 36. The VELCRO portions 40 and 42 are attached to the side support member 18 or 20. As shown in FIG. 7, these straps 34 and 36 may be tightly drawn around the lower leg of the user using the VELCRO loop material so that the ankle brace 16 securely and firmly supports the ankle.

The ankle brace 16 includes, in addition to the strap arrangement set forth above, a counter strap 60 which is similar in construction to the bottom strap 33. Specifically, the counter strap 60 may include a cushioning pad 61 and an inner surface covered with VELCRO loop material 62 and with the counter strap 60 passing through double openings 64 in the side support member 18 and double openings 66 in the other side support member 20. An additional piece of VELCRO loop material 67 is attached to side support member 18, and another piece of VELCRO loop material 67 is attached to side support member 20. With this arrangement the counter strap 60 may be adjusted in a similar manner to the bottom strap 33 to prevent the back portion of the side support means 18 and 20 from twisting or flexing outward at the lower end of the ankle brace 16 to compress the distal ⅓ to ½ of the brace.

The ankle brace may incorporate a lace fastening means similar to that set forth in detail in Grim, U.S. Pat. No. 4,844,094 to insure that the side supports 18 and 20 do not twist or flex outward and to more properly stabilize and compress the ankle against inversion, eversion and anterior subluxation. It is preferred, as shown in FIG. 7, that the lace fastening arrangement in the present invention comprises a hole or slot 70 and 72 integrally molded at the bottom end of each side support member 18 and 20. It is to be appreciated, however, that other attachment means such as those set forth in the U.S. Pat. No. 4,844,094 may be used.

FIGS. 1 and 2 illustrate an inflatable bladder and pump arrangement. The foot pump 26 is comprised of an open cell foam and or a flexible hollow or curved resilient material (such as rubber or plastic), which when compressed offers an increased pressurization of the entrapped fluid within its support membranes 27. The foot pump 26 is characterized by a variety of strategically-placed weld lines 80 which create channels through which fluid transfer can take place between the pump 26 and the inflatable bladders 22 and 24.

Other welded "darts" 82 may also be used which will aid in reducing the thickness in certain areas of the pump 26 to enhance comfort. The pump 26 may be constructed by welding in a foam of a thickness or space provided by the surrounding semi-enclosed pump material, preferably urethane or some other resilient material, whereby the foam is placed in a compressed state initially and when further compressed by the user's foot will be more resilient and recover quicker than if not compressed. The foot pump 26 is approximately three and one-half inches long and three inches wide.

In the ankle brace 16 the two main inflatable bladders 22 and 24 are interconnected with the foot pump 26. In this case, the two bladders 22 and 24 and the pump 26 are formed with one welding process and may be considered one member but is not so limited, and may include bladders which are connected to the pump by other fluid transfer means such as with tubes or valves.

As shown in FIGS. 1, 2, 3 and 8, the main bladders 22 and 24 each have inlet valves 84 and 86, which can be flap-type valves. In such a valve, air drawn in (entering the bladders 22 and 24) forces the valve's sealing flaps, which are normally biased together, apart which allows the air to flow through the valve. Air forced in a direction opposite to the air drawn in (exiting the bladders 22 and 24) forces the flaps together thereby creating a substantially airtight seal. Other types of valve arrangements may be used such as an air pressure release and bleed valve or inlet valves.

Thus, as shown in FIG. 4, the main bladders 22, 24 become inflated when air is directed through their valves 84, 86. The bladders 22, 24 expand a maximum width of approximately two and one-half inches. The preferred length of each main bladder 22, 24 is approximately ten and one-half inches long and is approximately three and three-quarters inches wide. As also shown in FIG. 4, the walls 87 of bladders 22, 24 are constructed of a non-porous resilient material, such as LYCRA fabric coated with or bonded to a thin layer of urethane. Each wall 87 is approximately 0.015 inch (15 mils) thick and is capable of stretching under force to allow the bladders a variety of widths to accommodate a wider foot base. Further, a fabric coating 88, for example, Nylon-Lycra, may be laminated to the plastic film that makes up the bladders 22 and 24 to allow the skin to breathe and to increase comfort to the user. This fabric coating 88 may be approximately 0.002 inch (2 mils) thick.

FIG. 5 shows a portion of the bladder that includes additional foam padding 89 which is located at the bottom half of each main bladder 22, 24. This padding 89 is about five inches in length and provides further comfort to the region surrounding the ankle.

As shown in FIGS. 1, 2 and 3, two more smaller inflatable bladders 30, 32 may be placed distally upon the main inflatable bladders 22, 24 to provide cushioning and support as well as protect the injured limb from the rigid support shell should either of the main bladders 22 or 24 puncture. Alternatively, these additional bladders 30 and 32 may also be made to pulsate and the longer main bladders 22, 24 may serve as non-pulsating protective membranes. The smaller bladders 30, 32 may be comprised of the same material and include the same valve arrangement as the main bladders 22, 24.

The shorter additional bladders 30, 32 extend from the bottom of the main bladders 22, 24 to about halfway up towards the uppermost portion of the main bladders 22, 24. The outside surface of each bladder 22, 30, 24 and 32 has a VELCRO portion 90 attached to it in order to affix the support member 18 and 20 to the bladders. It should be further mentioned that all bladder arrangements 22, 30, 24 and 30, are preferably distributed with a certain amount of preinflation.

FIGS. 9 through 18 illustrate the principles of this invention and show alternate side support members 18 and 20, which may be used in the assembly of FIG. 7.

FIGS. 9 and 10 show a support member 20 which is constructed of a rigid polypropylene in one embodiment. Support member 18 may be constructed in an identical manner to support member 20. The support member 20 is slightly curved (see FIG. 10) to better hug and support the ankle. The support member 20 also has one or more holes 19 for positioning the part into a mold during the overmolding process. In the overmolding process, one material is first molded, and then a second, a more flexible and resilient material is molded over the first molded piece. The hole(s) 19 is/are also used for venting any heat that accumulates within the entire ankle brace 16, and in some cases, for securing the resilient material to the support member 20. The bottom perimeters of each support member 18, 20 are covered with a flexible padded material 95, preferably vinyl, rubber, or synthetic rubber such as SANTOPRENE manufactured by Monsanto, KRATON manufactured by Shell, or ALORYN manufactured by DuPont, in order to prevent each side support member 18, 20 from cutting into the user's lower leg or from puncturing the bladders 22, 23, 24 and 25, and most importantly, to improve the fit of each side support members 18, 20 around the user's lower leg. The material used is preferably a TPE (Thermoplastic Elastomer) and a preferred selection thereof is RIMFLEX. Support members 18, 20 may be manufactured of a suitable rigid or semi-rigid material such as Nylon or glass reinforced nylon by DuPont or High Density Polyethylene (HDPE) made by Dow Chemical Co. The primary job of the overmold (flexible material 95) is to prevent pinching.

Flexible resilient or padding material 95 may be bonded to support members 18, 20 by either a permanent adhesive, semi-permanent adhesive or solvent. The flexible padded material 95 may also be formed in place around support members 18, 20, or may be thermally bonded in place. The padding material 95 may, for example, be rubber or other similar material. The preferred method for making this resilient edge is to overmold the softer material onto the shell. When molded in that manner, there is no need for additional adhesives or even the additional labor step of assembly.

Openings, such as slots 51 and 65, may be included in support member 20 in order to allow straps to be passed through the side support member. In addition, slots 101, 103, 105, 107, 109, and 111, or others, may be provided to allow mechanical interlocking of the resilient or padding material 95 to secure padding material 95 to side support member 20. Slots 101, 103, 105, 107, 109 and 111 may be replaced by suitable grooves, channels or other suitable interlocking arrangements which can be readily mated with the resilient material 95, which is positioned against side support member 20. In this manner, the resilient material and the side support member may be interlocked without requiring the use of additional mechanical fasteners such as straps, tape, cement or the like. While cement or heat bonding can be used to supplement the mechanical interlocking, a preferred method for attachment is overmolding to the mechanical interlocking members.

Additionally, the inner surface of each side support member 18 and 20 may include a strip or strips of VELCRO loop 91 to allow the side supports a means of attaching themselves to the VELCRO portions 90 of each bladder or other padding.

FIGS. 11 and 12 show the support member 20' similar to the support member shown in FIGS. 9 and 10 except that the support is secured on top of a flexible cushioning material 95 having a slightly larger area than the side support member 20 but is substantially the same shape as the side support, more securing holes 19 are present, and the slots 51, 65, 101, 103, 105, 107, 109, and 111 have been removed. Slots 101, 103, 105, 107, 109 and 111 are mechanical locking slots for the resilient material 95 during the overmolding process.

Alternative embodiments shown in FIGS. 13–14 and 17–18 illustrate side supports 20" and 20"', respectively, similar to the side supports shown in FIGS. 9–12, except that the side support member is reduced in mass by forming a structural frame instead of a solid surface. The structural support consists of peripheral members 116 (FIGS. 13 and 14) and 116' (FIGS. 17 and 18) which extend around the perimeter on the side support member 20. Single support members 20" and 20"' are illustrated; however, the support members for the opposing side of the ankle are constructed in the same manner. In FIGS. 13 and 14, openings 110 and 112 are present in the upper and lower portions of the support member 20", and a lateral structural member 114 is located between openings 110 and 112 to add strength to the framework 116.

Figure 17:
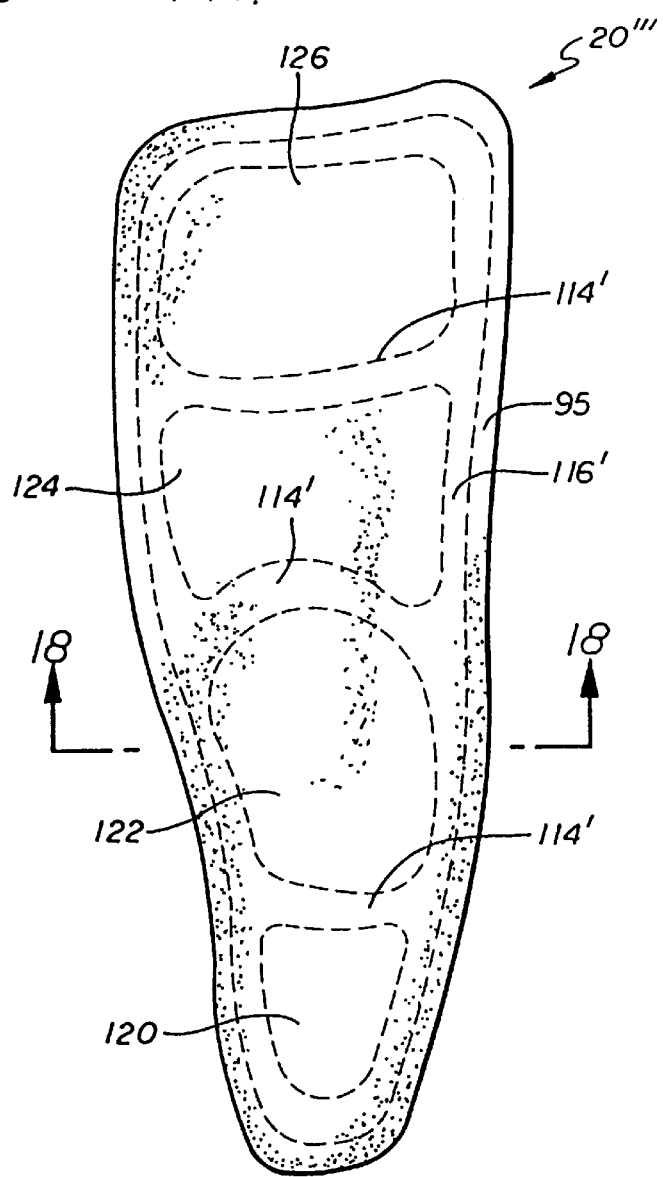
FIG. 17 is a side view of a further alternative embodiment of a side support member of the present invention.
Figure 18:
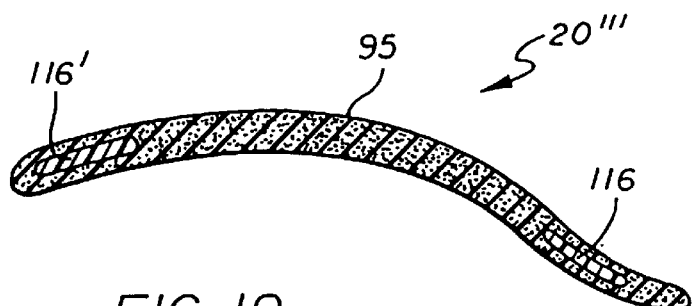
FIG. 18 is a transverse cross-sectional view of the embodiment shown in FIG. 17, taken along line 18—18 of FIG. 17.

In FIGS. 17 and 18, structural members of the three transverse members 114' add strength to the perimeter frame 116 of the side support member 20"". Thus, additional structural members can be employed to increase the structural strength and integrity of the side support member 20"' without significantly increasing the weight of this support member. The configurations shown in FIGS. 13 and 17 have a weight which is reduced from the weight of side supports as shown in FIGS. 9–12, because of the material which is removed in forming openings 110, 112, 120, 122, 124 and 126. This configuration also allows the reduction in pressure in specific areas such as the malleoli or anklebones, see area 112 in FIG. 13, and area 122 in FIG. 17.

As shown in FIGS. 13 and 17, the entire perimeter of support member 20 is covered with a flexible resilient or padded material 95 in order to prevent the support members 18 and 20 from cutting into the user's lower leg, or from puncturing the bladders 22, 23, 24 and 25, and to improve the fit of each side support member 18 and 20 around the user's lower leg.

The more rigid molded material as shown in FIGS. 9–14 may be constructed of new overmolding technique as earlier described. This material may readily replace the use of a two piece assembly shown in FIGS. 9–18. This technique would be especially useful when employed with the configuration shown in FIGS. 9–12. The flexible material 95 in a preferred embodiment is an overmolded material and not a separate piece construction.

Figure 16:
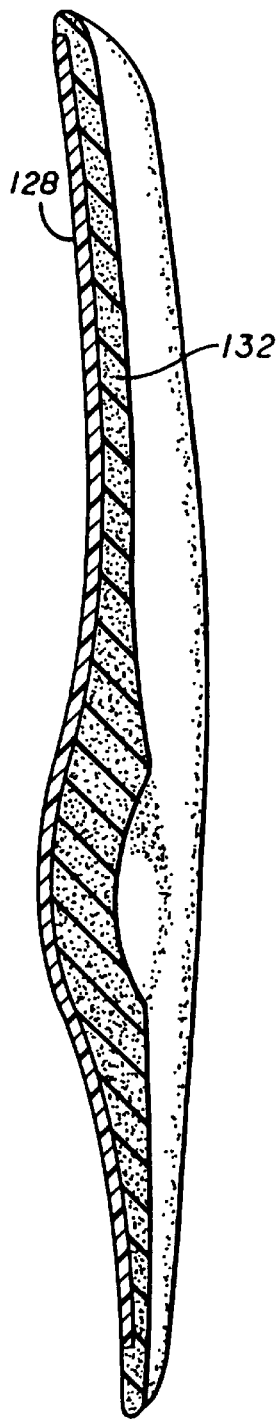
FIG. 16 is a longitudinal cross-sectional view of the embodiment shown in FIG. 15.

In the embodiment shown in FIGS. 15 and 16, side support member 128 is formed to accommodate the "bulge" of the ankle of the wearer. Flexible or resilient material 132 is shaped or formed to complement the shape of side support member 128 and provide padding between the ankle of a wearer and side support member 128. The showing of FIG. 15 is a view of the outside 130 of the ankle brace of FIG. 16. Flexible material 132 may be formed integrally with side support member 128, or may be integrally bonded thereto, as shown in FIG. 16. The material 132 may be a soft vinyl foam or a thermoplastic elastomer of the type sold under the trademark SANTOPRENE.

In the embodiments shown in FIGS. 9 and 10, a single plastic body having a more rigid central portion and grading into a more flexible plastic around the outer edges of side support member 20 may be employed. The resilient material 95 is the more flexible material overmolded to the more rigid plastic. The resilient material 95 may extend over the entire interior surface thereby eliminating the need for any additional padding. If this does not extend over the interior surface, additional padding would be required. This may result in a side support member which has a uniform thickness and is more flexible towards the edges of the side support member 20 and more rigid towards the center. It is recognized that this technique may be applied to all of the edges of side support member 20 in the configurations of FIGS. 9–18.

In another embodiment of the present invention, either side support member 18 or 20 may be applied to the ankle of the wearer by the use of one or more straps fastening a single side support member to the leg of the user. This configuration can be used to treat less severe ankle injuries while reducing the weight and bulkiness of the brace which must be worn by the user. Preferably the side support member is located on the side of the leg of the wearer to provide the greatest support to the ankle, and immobilize the ankle against particular undesired rotation based on the nature of the ankle injury.

For many users, it is additionally desirable to place a padded material between the ankle and the straps that surround the lower leg, holding the side support member 18 or 20 against the lower leg of the wearer.

The operation of the ankle brace 16 in conjunction with air bladders would be as follows: the bladder and pump arrangement is attached to the inside of the side supports 18, 20. If the brace 16 has been previously used, the bottom strap 33 and the counter strap 60 would already have been adjusted. If not, the wearer would position the side supports 18, 20 to both sides of the ankle, and then after the side supports 18, 20 are properly positioned, the ankle brace 16 would be held in place using the strap members 34, 36. The bottom strap 33 would then be adjusted by peeling the VELCRO loop material 35 back from the corresponding VELCRO material 54 and 56 and pulling up both sides of the strap 33 until the bottoms of the side supports are firmly in position. The ends of the strap 35 would then be firmly pressed down on the VELCRO material 54 and 56 to lock the strap in 33 in position. Similarly, the counter strap 60 would be adjusted to pull the back lower end of the side supports 18 and 20 together above the heel.

The shoe would now be fitted over the entire ankle brace 16, as shown in FIG. 7, and the laces laced through the holes 70 or in other fastening means located at the lower end of the side supports 18, 20. The laces would then be pulled tight and tied, again as shown in FIG. 7, so that the ankle brace 16 is firmly in position. Subsequently, the bladders 22, 30, 24 and 32 are inflated to their therapeutically desired pressure by using, for example, an attachable hand-held pump.

Therefore, while in use, the fluid within the pressurized ankle support bladders 22, 30, 24 and 32 and the interconnected preinflated foot pump is displaced back and forth between either the main bladders 22, 24 and/or the shorter bladders 30 and 32 thereby creating a pulsing action which provides a massaging compression effect that helps reduce swelling and atrophying and increases venous and lymphatic return throughout the lower leg, while effectively preventing inversion, eversion and anterior subluxation of the ankle.

Figure 19:
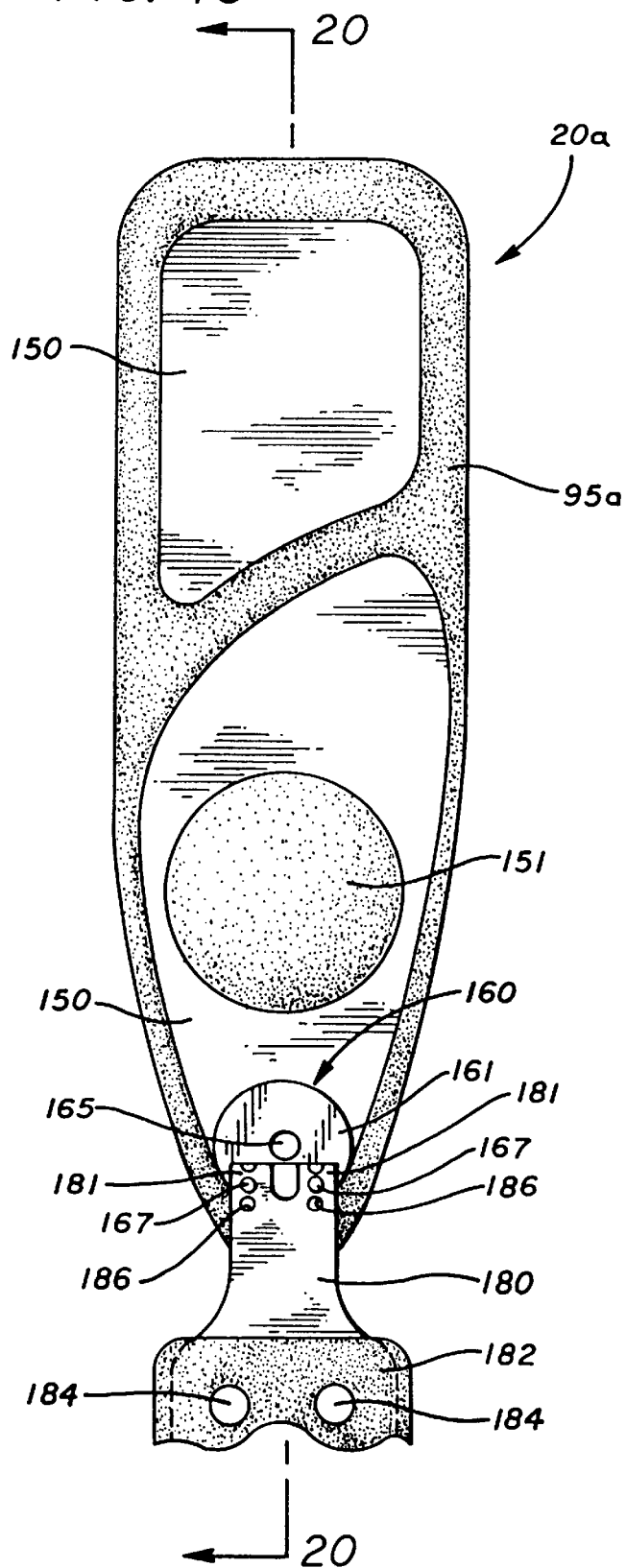
FIG. 19 is a side view of another alternative embodiment of a side support member.
Figure 20:
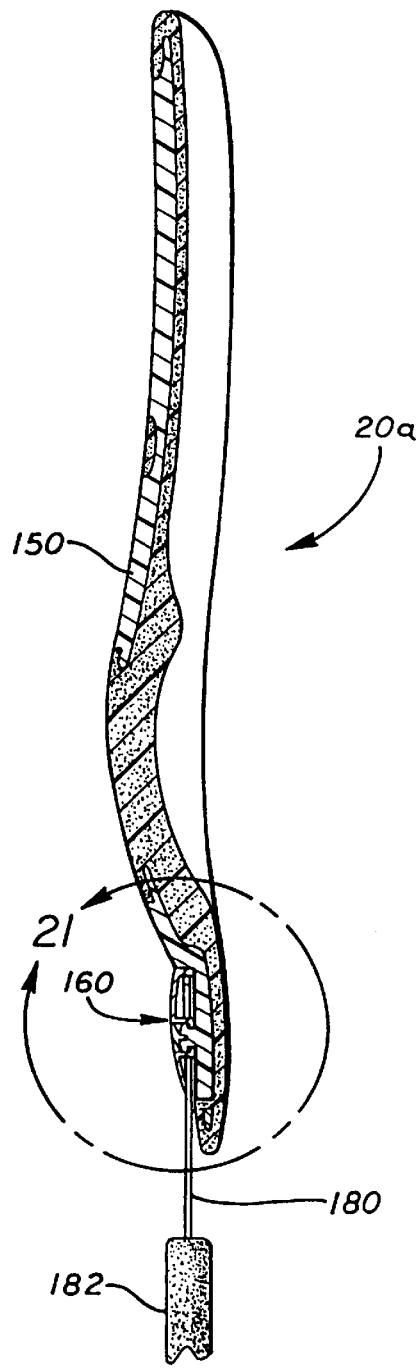
FIG. 20 is a longitudinal cross-sectional view of the side support taken along line 20—20 of FIG. 19.
Figure 21:
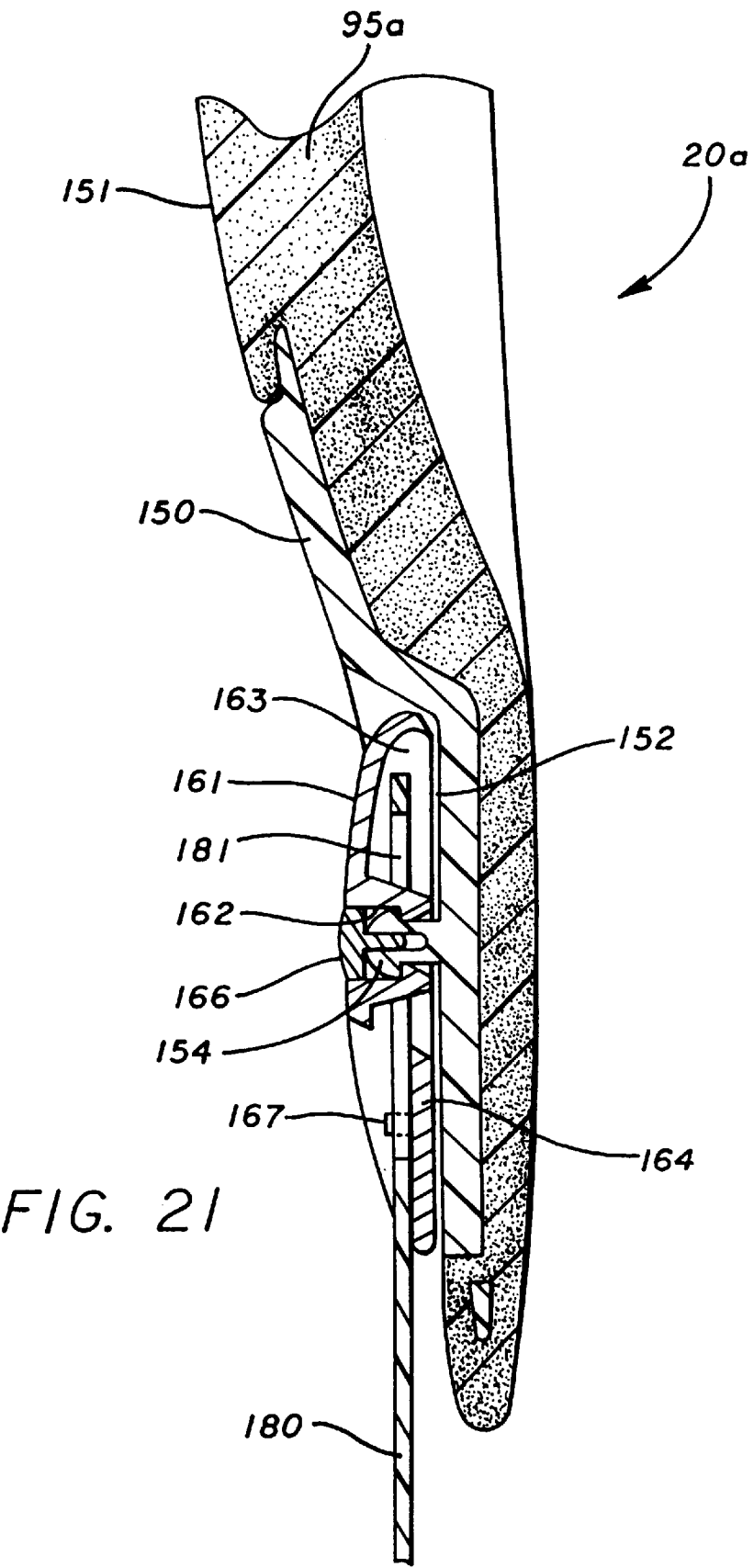
FIG. 21 is an enlarged detail view of the section defined by circle 21 of FIG. 20.

Another alternative embodiment shown in FIGS. 19–21 illustrates side supports 20a, similar to the side supports shown in FIGS. 9–15, that includes at the lower end of the side support frame 150, a pivot disc 160 with attachment pins 167 to allow the heel strap 180 to be adjustably attached to the side supports 20a.

FIGS. 19–20 show that in this implementation, the side support member 20a is formed with a structural frame 150 which surrounds but does not cover the ankle or malleolus area 151. The ankle area 151 is only covered by the resilient flexible material 95a.

FIGS. 19 and 21 show a pivot disc 160 mounted to the lower end of a side support frame 150 at the pivot point 165. The lower end of a side support frame 150 comprises a circular recess 152 to receive the circular pivot disc 160. The pivot disc 160 may be coupled to the frame 150 using a mechanical interlock or a cap 166. For a mechanical interlock coupling, the recessed area 152 of the frame 150 has a protruding pin 154 at the center of the recessed area with which an opening 162 in the center of pivot disc 160 is interlocked by mating shoulders on the pin 154 and the opening 152. A cap 166 may serve as a supplemental coupling to secure the pivot disc 160 to the side support frame 150.

As shown more clearly in FIG. 21, the pivot disc 160 may have an upper portion 161, which may be formed to create a cavity 163 between it and the recessed area formed by the portion of the side support frame 152, and a lower portion 164 to which pins 167 are affixed. In this implementation, the cavity may function as clearance to receive the ends of the heel strap 180 which have been divided into two strips 181 with holes 186 to be selectively coupled to the pins 167.

The heel strap 180 is made of flexible resilient material such that the effective length of the heel strap can be adjusted to fit the width of the heel being protected. FIGS. 19 and 21 show the heel strap 180 and the heel pad 182 that may be attached to the strap to increase the cushioning of the heel. Holes 184 may be used to mechanically interlock the strap 180 and the pad 182 by molding the pad through the holes. Each end of the heel strap 180 may be slotted to form two strips 181 which straddle the pivot point 165. Each strip 181 contains several holes, aligned with corresponding holes of the other strip at the same end, which are used to adjustably attach the heel strap 180 to pivot disc 160.

Instead of the pins 167 and the holes 186, VELCRO hook and loop pads may be used to adjustably attach the heel strap 180 to the pivot disc 160.

While FIGS. 1–8 relate to the combination using bladders, it is to be understood that the arrangements of FIGS. 9–18 may be employed using gel or foam rubber pads, for example, between the side members and the ankle, or in some cases with no additional padding.

Figure 26:
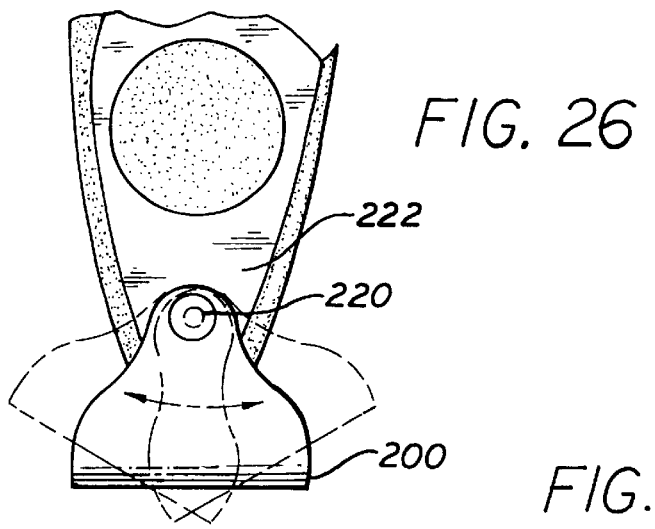
FIG. 26 is a side view of an embodiment of a side support member illustrating the principle of the present invention.
Figure 27:
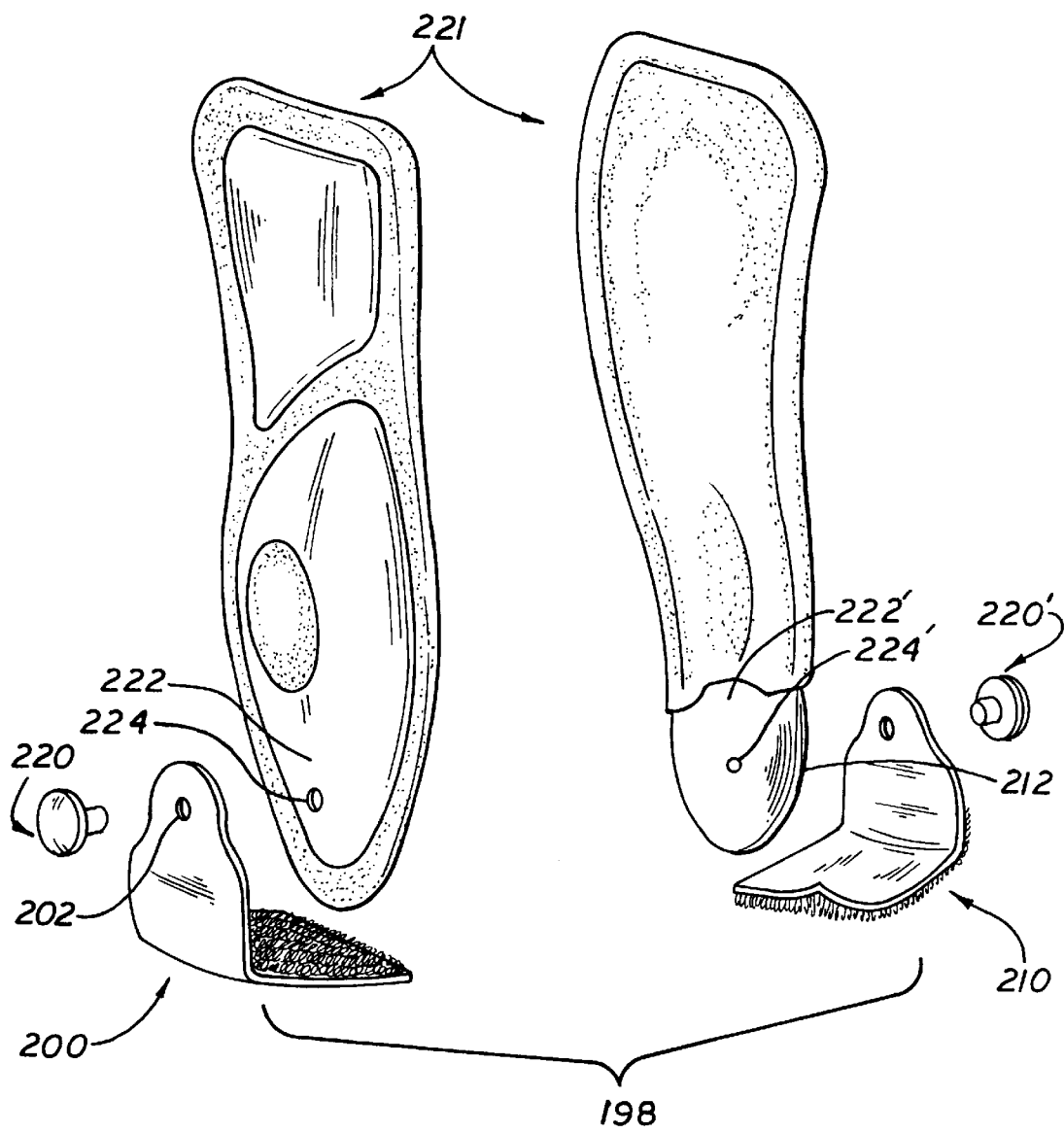
FIG. 27 is an exploded perspective view of the embodiment of FIGS. 22 and 24 showing the side supports and heel straps in their relative positions.
Figure 30:
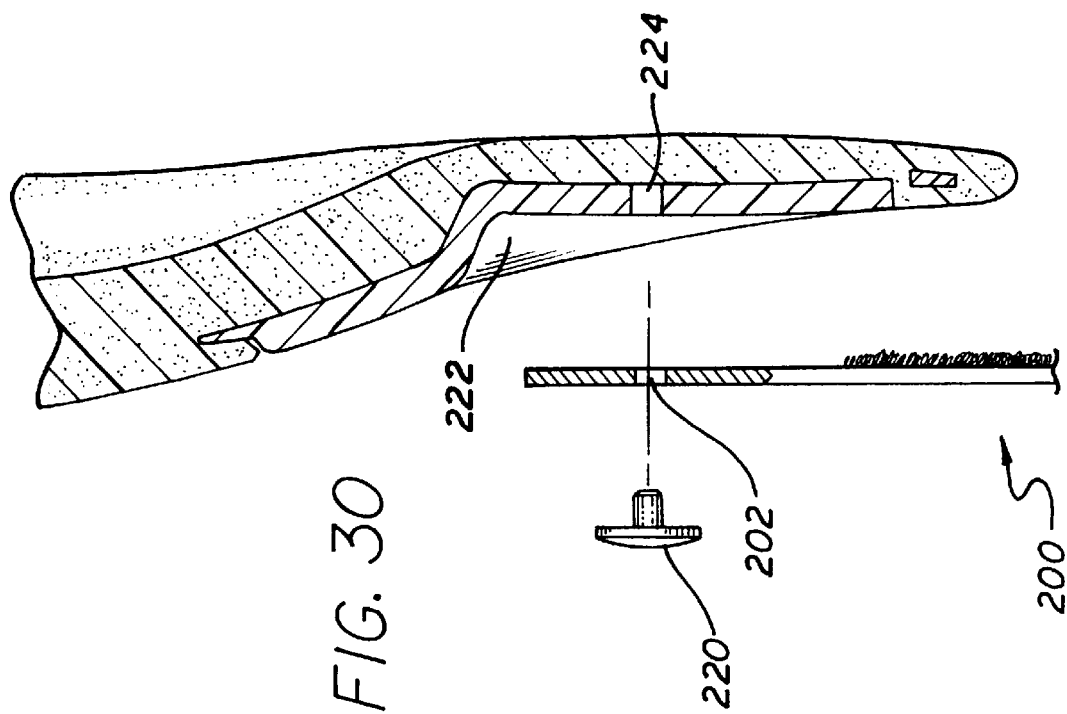
FIG. 30 is an exploded cross-sectional view illustrating a heel strap coupling to a side support of FIG. 28.
Figure 28:
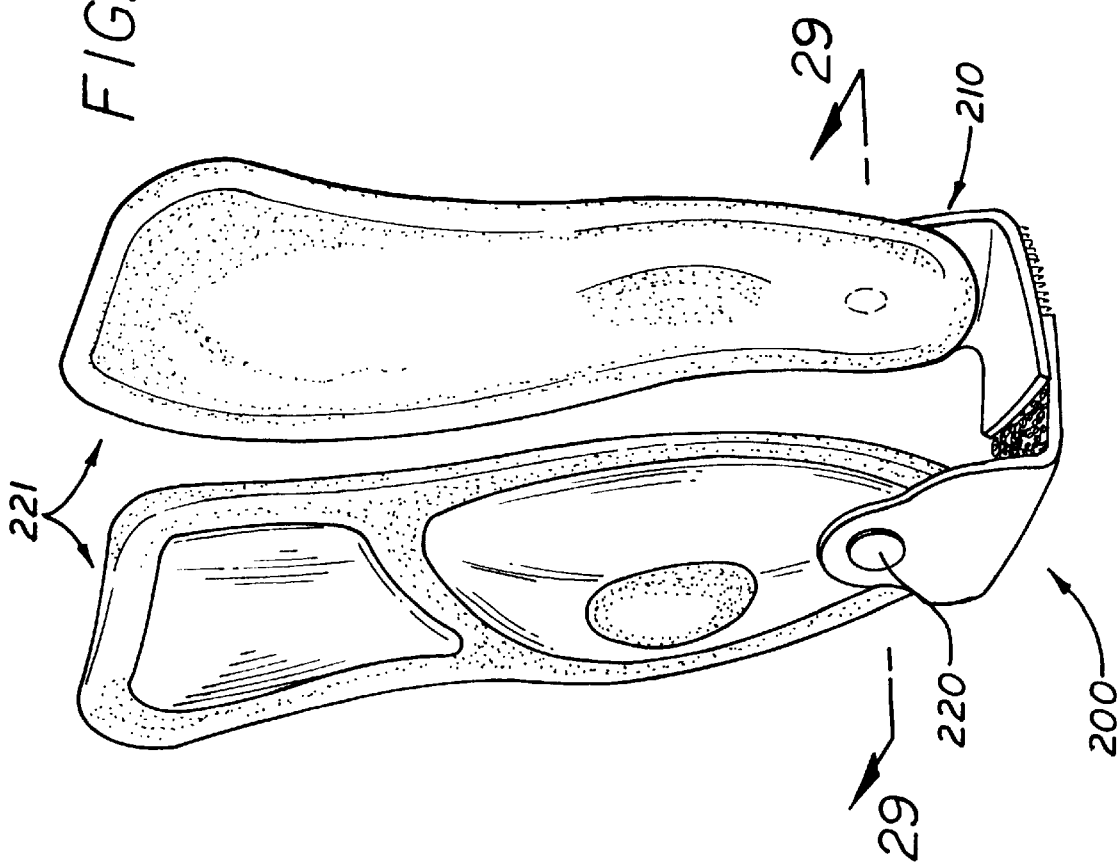
FIG. 28 is an assembled perspective view of the side supports and heel straps in FIG. 27.

Focus now turning to the heel strap, FIGS. 22–29 illustrate another alternative embodiment for an assembly of heel straps 198 that is pivotally attached to side support member 221, as shown more clearly in FIG. 27. According to this embodiment, side supports 221 are similar to the side supports shown in FIGS. 9–15, that have a lower side support member 222 with a hole 224. The assembly 198 includes a first strap 200 and a second strap 210, as shown more clearly in FIGS. 22–25. The first strap 200 is preferably divided into two regions, namely a neck region 204 and a body region 206. The neck region 204 has a hole 202 at the top thereof to allow a pin 220 (as shown in FIG. 30) to engage through both of the holes 202 and 224, thereby pivotally attaching the first strap 200 to the lower side support member 222. Referring to FIG. 29, the pin 220 has an inner pin button 225, which is installed by means of a mechanical snap fit whereby the pin 220 mates with the pin button 225 in an interlocking fashion. The pin button can also be sonic welded to the pin 220, or vice versa. In addition or alternatively, adhesives, solvents or heat can be used to bond the two members together. Likewise, the second strap 210 has two regions 214 and 216, with a hole 212. And the second strap is pivotally attached to the lower side support member 222' by the pin 220' that engages through both of the holes 212 and 224'. FIG. 26, by way of example, illustrates the range of pivot movements of the strap that is attached by the pin 220.

According to this alternative embodiment, the assembly of heel strap 198 is formed by coupling the first strap 200 with the second strap 210. In this regard, the body region 206 is preferably covered with a VELCRO loop material 208 and the body region 216 is preferably covered with a VELCRO hook material 218. As illustrated by way of example in FIG. 31, the first strap 200 is coupled to the second strap 210 by securing the VELCRO hook material 218 over the VELCRO loop material 208 together, which forms a bonding area 230. Preferably, the bonding area 230 between the VELCRO loop and the VELCRO hook material may vary, so that the assembly may have its effective length being adjustable to accommodate for different heel widths of different patients or different desired fits. At the same time, even at its longest length, i.e. its smallest bonding area 230, there is sufficient bonding area to hold the straps 200 and 210 together. As illustrated by way of example in FIG. 29, the assembly of heel strap 198 is coupled to the lower side supports 222 and 222'. Here, the heel straps 200 and 210 are pivotally attached to the side supports by the pins 220 and 220', and effective length of the assembly 198 is adjustable by varying the bonding area 230.

Another alternative embodiment of an assembly of heel strap 261 is shown in FIGS. 40 and 41. According to this embodiment, the assembly 261 includes a linking member 260 and a pair of straps 262. The pair of straps 262 are similar to the strap 210 in FIG. 24, in that both have the VELCRO hook material on the body regions. However, a linking member 260 is provided covered with a VELCRO loop material so that it may bond with the pair of straps 262, as shown more clearly in FIG. 41. And again, the assembly of heel straps 261 is adjustable by varying the bonding areas between the VELCRO loop material and hook material to accommodate for the different heels and different desired fits of different patients.

A further alternative embodiment of an assembly of heel strap 271 is shown in FIGS. 42 and 43. The assembly 271 includes a linking member 272 and a pair of straps 270. This embodiment is similar to the embodiment illustrated in FIGS. 40 and 41, except here, instead of employing the VELCRO hook material and loop material pads, the linking member 272 has a plurality of upright members 274, and the pair of straps 270 has a plurality of open slots 276, which are used to couple the pair of straps 270 and the linking member 272 together, as shown more clearly in FIG. 42. Preferably, the open slots 276 are symmetrically aligned to the plurality of upright members 274 so they may easily engage together, as illustrated in FIG. 43. The assembly 271 has its effective length being adjustable by engaging the upright members 274 into the open slots 276 that may best accommodate the heel of the patient. The principle illustrated in this embodiment is similar to adjusting the size of a baseball cap. For example, many baseball caps have a pair of straps on the back for adjusting the size, one strap generally has a plurality of upright members and the other strap has a plurality of open slots, where any of the upright members may be engaged along any of the open slots, so that the size of the baseball cap can be adjusted for a particular user.

It should be noted that various changes may be made without departing from the spirit and scope of the invention. For example, in the alternative embodiment shown in FIGS. 40 and 41, the linking member 260 and straps 262 may have reverse VELCRO hook and loop properties, i.e. instead of linking member 260 being covered with VELCRO loop material it may be covered with VELCRO hook material. Likewise, in FIGS. 42 and 43, the linking member 272 may have open slots instead of upright members.

Focusing now on the pin mechanism, FIGS. 32–39 illustrate another alternative pin mechanism for pivotally attaching the heel straps to the side supports. As illustrated by way of example in FIGS. 33 and 35, the straps 240 and 250 are similar to the straps 200 and 210, respectively, except that the holes 202 and 212 are replaced by elongated tapered pins 242 and 252, respectively, which take the place of pins 220 and 220'. Similarly, the strap 240 has a VELCRO-type loop material 244 and the strap 250 has a VELCRO hook material 254. Also, as shown more clearly in FIGS. 37 and 38, the straps are pivotally attached to the side supports by engaging the nose 242 through the hole 254. Thereafter, the nose 242 is preferably capped by an ultrasonic weld 256, as shown more clearly in FIG. 38. The nose can also be capped by heat staking, which is a process that involves heating the end of the nose and pressing it with a shaped tool to mushroom the end out, similar to ultrasonic staking. As illustrated by way of example in FIG. 39, the assembly of heel straps are pivotally attached to the side supports by the nose 242 and pin 252 and capped at the ends by the ultrasonic welds 254 and 256.

With respect to material, the assembly of heel straps is preferably made of flexible resilient material, such as hook and/or loop materials bonded to the rigid plastic pin. Similarly, baseball cap type straps can be integrally molded with a protruding plastic pin, thereby eliminating a manufacturing step. In addition, caps with protruding plastic pins can be molded directly onto the hook and loop material, effectively making them one piece to be assembled as such. The material should form comfortably around the heel of a patient but be strong enough to resist stretching from the tension that may occur from walking by the patient so that the effective length can be maintained once adjusted by the user.

Although the invention has been described with reference to particular embodiments, it is to be appreciated that other adaptations and modifications may be used without departing from the spirit and scope of the present invention. For example, in FIG. 8 a heel cup 100 which may or may not be inflatable may be included to provide further support to the ankle region. Also, a possible extra bladder surrounding the ankle may be incorporated into the brace 16 to contain gel or water, with or without foam, for hot or cold therapy. In addition, the heel strap may have a series of central holes which may encompass the pivot point with the length of the strap being adjustable by selecting different holes through which the pivot structure extends. Accordingly, the present invention is not limited to the constructions precisely as shown in the drawings or described in the detailed description.

What is claimed is:

1. An ankle brace, comprising:
    a pair of side supports, said side supports being configured to fit about a lower leg of a patient and to encase both sides of an ankle of the patient; and
    a flexible heel strap assembly pivotally attached at lower ends of said side supports and extending between said lower ends, said assembly having its effective length being adjustable to accommodate for different heel widths or fits of patients.

2. An ankle brace as defined in claim 1, wherein said flexible heel strap assembly has a pair of flexible heel straps, which are adapted to couple at free ends thereof.

3. An ankle brace as defined in claim 2, wherein one of said pair of straps has hook material and other of said pair of straps has loop material adapted to releasably mate with said hook material.

4. An ankle brace as defined in claim 2, wherein one of said pair of straps has a plurality of upright elements and the other said pair of straps has a plurality of open slots, said pair of straps are coupled by engaging said upright elements into said open slots.

5. An ankle brace as defined in claim 1, wherein said flexible heel strap assembly comprises a pair of flexible heel straps and an intermediary linking member which is adapted to couple at opposite ends thereof to said pair of flexible heel straps.

6. An ankle brace as defined in claim 5, wherein said pair of flexible heel straps has a hook material at the free ends to connect adjustably to said intermediary linking member having a loop material adapted to form the assembly which can accommodate for different heel widths of different patients.

7. An ankle brace as defined in claim 5, wherein said pair of flexible heel straps has a loop material at the free ends to connect adjustably to said intermediary linking member having a hook material adapted to form the assembly which can accommodate for different heel widths of different patients.

8. An ankle brace as defined in claim 5, wherein said pair of flexible heel straps has a plurality of upright elements at the free ends and said intermediary linking member has a plurality of open slots adapted to adjustably connect to said plurality of upright elements to form the assembly to accommodate for different heel widths or fits of patients.

9. An ankle brace as defined in claim 5, wherein said pair of flexible heel straps has a plurality of open slots at the free ends and said intermediary linking member has a plurality of upright elements adapted to adjustably connect to said plurality of open slots to form the assembly to accommodate for different heel widths or fits of patients.

10. An ankle brace as defined in claim 5, wherein said flexible heel strap assembly has a plurality of intermediary linking members adapted to connect adjustably to said pair of straps to form the assembly to accommodate for different heel width of different patients.

11. An ankle brace as defined in claim 1, wherein said side supports at lower ends each has an opening hole, said flexible heel strap assembly at both of its ends has an opening hole, wherein said assembly is pivotally attached at lower ends of said side supports by respective pins engaging through both said assembly and side support holes.

12. An ankle brace as defined in claim 11, wherein each of said pins is capped by an ultrasonic weld.

13. An ankle brace as defined in claim 11, wherein a cap snap fits to each of said pins.

14. An ankle brace as defined in claim 11, wherein said pins are capped by heat staking.

15. An ankle brace as defined in claim 1, wherein said side supports at lower ends each has an opening hole, said flexible heel strap assembly at both of its ends is pivotally attached at lower ends of said side supports by respective pins, said pins snap fitting to said side supports through said opening holes.

16. An ankle brace as defined in claim 1, wherein said side supports at lower ends each has a hole, said flexible heel strap assembly at both of its ends has a pin, wherein said assembly is pivotally attached at lower ends of said side supports by said respective pins engaging through each said side support hole.

17. An ankle brace as defined in claim 16, wherein said pin is capped by an ultrasonic weld.

18. An ankle brace as defined in claim 16, wherein said pin is capped by a heat staking.

19. An ankle brace as defined in claim 16, wherein said pin is directly injection molded onto said flexible heel strap assembly.

20. An ankle brace as defined in claim 16, wherein a cap is formed from said pin by an ultrasonic weld.

21. An ankle brace as defined in claim 16, wherein said pin is a long protruding member.

22. An ankle brace as defined in claim 1, wherein said assembly has at least two straps, at least one of said straps has a plurality of regions, at least one of said regions being adapted for adjustably connecting to said other strap, and said at least one region being adapted to hold a pin.

23. An ankle brace as defined in claim 1, wherein said assembly has at least two straps, at least one of said straps has a plurality of regions, at least one of said regions being adapted for adjustably connecting to said other strap, and said at least one region having a hole for receiving a pin.

24. A method of bracing an ankle, comprising the steps of:
positioning a pair of side supports about a lower leg of a patient, with a flexible heel strap assembly pivotally attached at lower ends of said side supports;
extending said flexible heel strap assembly across the patient's heel; and
adjusting an effective length of said flexible heel strap assembly to accommodate for different heel widths of different patients.

25. A method according to claim 24, wherein said adjusting and assembling steps include:
releasing two straps from said flexible heel strap assembly; and
assembling said flexible heel strap assembly to accommodate for different heel widths or fits of patients.

26. A method of bracing an ankle, comprising the steps of:
positioning a pair of side supports about a lower leg of a patient, with a flexible heel strap pivotally attached at each lower end of said side supports;
positioning said flexible heel strap from each said side supports across the patient's heel;
adjusting said flexible heel strap from each said side supports to have a combined effective length to accommodate for different heel widths or fits of patients; and
assembling said flexible heel strap from each said side support at the combined effective length.

27. A method according to claim 26, wherein said adjusting and assembling steps including:
securing together said flexible heel strap from each said side supports along its respective ends.

28. A method according to claim 26, wherein said adjusting and assembling steps including:
positioning an intermediary linking member between said flexible heel strap from each said side supports; and
assembling said intermediary linking member to each of said flexible heel straps from each said side supports.

29. A method of bracing an ankle, comprising the steps of:
positioning a pair of side supports about a lower leg of a patient, with a flexible heel strap assembly pivotally attached at lower ends of said side supports;
extending said flexible heel strap assembly horizontally across said patient's heel; and
adjusting an effective length of said flexible heel strap assembly to accommodate for different heel widths or fits of patients.

* * * * *